(12) United States Patent
Stocker et al.

(10) Patent No.: US 12,140,514 B2
(45) Date of Patent: Nov. 12, 2024

(54) SENSOR AND METHOD FOR PERFORMING A REFERENCE MEASUREMENT WITH GUIDED THERMAL RADIATION

(71) Applicant: Infineon Technologies AG, Neubiberg (DE)

(72) Inventors: Gerald Stocker, Finkenstein (AT); Elmar Aschauer, Ledenitzen (AT); Ulf Bartl, Villach (AT); Thomas Grille, Nötsch (AT); Christoph Kovatsch, Finkenstein (AT); Thomas Krotscheck Ostermann, Velden am Wörthersee (AT)

(73) Assignee: Infineon Technologies AG, Neubiberg (DE)

( * ) Notice: Subject to any disclaimer, the term of this patent is extended or adjusted under 35 U.S.C. 154(b) by 302 days.

(21) Appl. No.: 17/658,554

(22) Filed: Apr. 8, 2022

(65) Prior Publication Data

US 2022/0381659 A1    Dec. 1, 2022

(30) Foreign Application Priority Data

Jun. 1, 2021   (EP) .................................... 21177166

(51) Int. Cl.
  *G01N 1/44*     (2006.01)
  *G01K 7/01*     (2006.01)
  *G01N 33/00*    (2006.01)
(52) U.S. Cl.
  CPC ................. *G01N 1/44* (2013.01); *G01K 7/01* (2013.01); *G01N 33/004* (2013.01)

(58) Field of Classification Search
  CPC ...... G01N 1/44; G01N 33/004; G01N 21/255; G01N 2201/0873; G01N 21/274;
  (Continued)

(56) References Cited

U.S. PATENT DOCUMENTS 7,709,795 B2 *   5/2010   Yamanaka ................ G01J 5/20
                                            250/338.1
10,345,227 B2 *   7/2019   Lavchiev ........... G01N 21/7703
(Continued)

FOREIGN PATENT DOCUMENTS

EP   0725269 A2   8/1996
EP   3715829 A1   9/2020
(Continued)

OTHER PUBLICATIONS

Green, William M.J., et al., "Silicon Photonic Gas Sensing", IEEE Optical Fiber Communications Conference and Exhibition (OFC), Mar. 3-7, 2019, 3 pages.

*Primary Examiner* — David J Bolduc
(74) *Attorney, Agent, or Firm* — Slater Matsil, LLP

(57) ABSTRACT

A fluid sensor for performing a reference measurement includes a support structure having a top main surface region; a thermal emitter on the top main surface region of the support structure; a first waveguide section and a first thermal radiation detector on the top main surface region of the support structure; and a cover structure on at least one part of the first waveguide section. The first waveguide section guides a first portion of the thermal radiation emitted by the thermal emitter to the first thermal radiation detector. The first thermal radiation detector detects the guided first portion of the thermal radiation for performing the reference measurement.

20 Claims, 12 Drawing Sheets

(58) Field of Classification Search
CPC ........ G01N 21/3504; G01K 7/01; G01K 7/02; G01K 7/00; G01K 7/16
See application file for complete search history.

(56) References Cited

U.S. PATENT DOCUMENTS

| | | | |
|---|---|---|---|
| 2007/0101800 A1* | 5/2007 | Stenberg | G01N 21/031 |
| | | | 250/343 |
| 2013/0081447 A1* | 4/2013 | Carter | G01N 21/05 |
| | | | 73/30.01 |
| 2014/0061677 A1* | 3/2014 | Jakoby | G01N 21/648 |
| | | | 257/E33.077 |
| 2017/0005220 A1* | 1/2017 | Kautzsch | H01L 31/173 |
| 2017/0059499 A1* | 3/2017 | Duraffourg | G01N 33/0036 |
| 2019/0154570 A1* | 5/2019 | Gylfason | G02B 6/1228 |
| 2020/0309686 A1 | 10/2020 | Grille et al. | |
| 2020/0309691 A1 | 10/2020 | Sakamoto et al. | |

FOREIGN PATENT DOCUMENTS

| | | |
|---|---|---|
| FR | 3056750 A1 | 3/2018 |
| WO | 2016208176 A1 | 12/2016 |
| WO | 2017008077 A1 | 1/2017 |
| WO | 2019115698 A1 | 6/2019 |

* cited by examiner

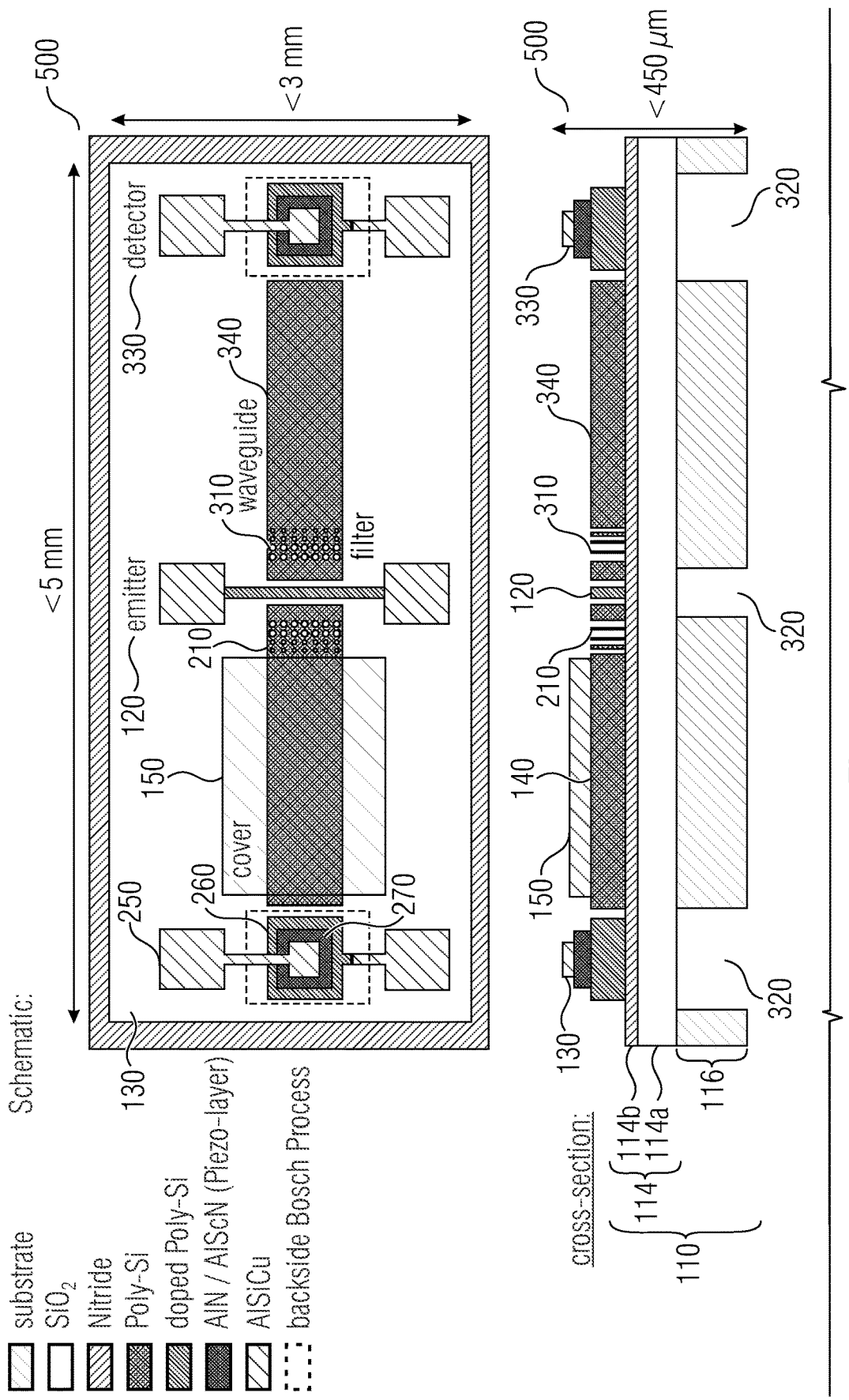
Fig. 5 (Part 1)

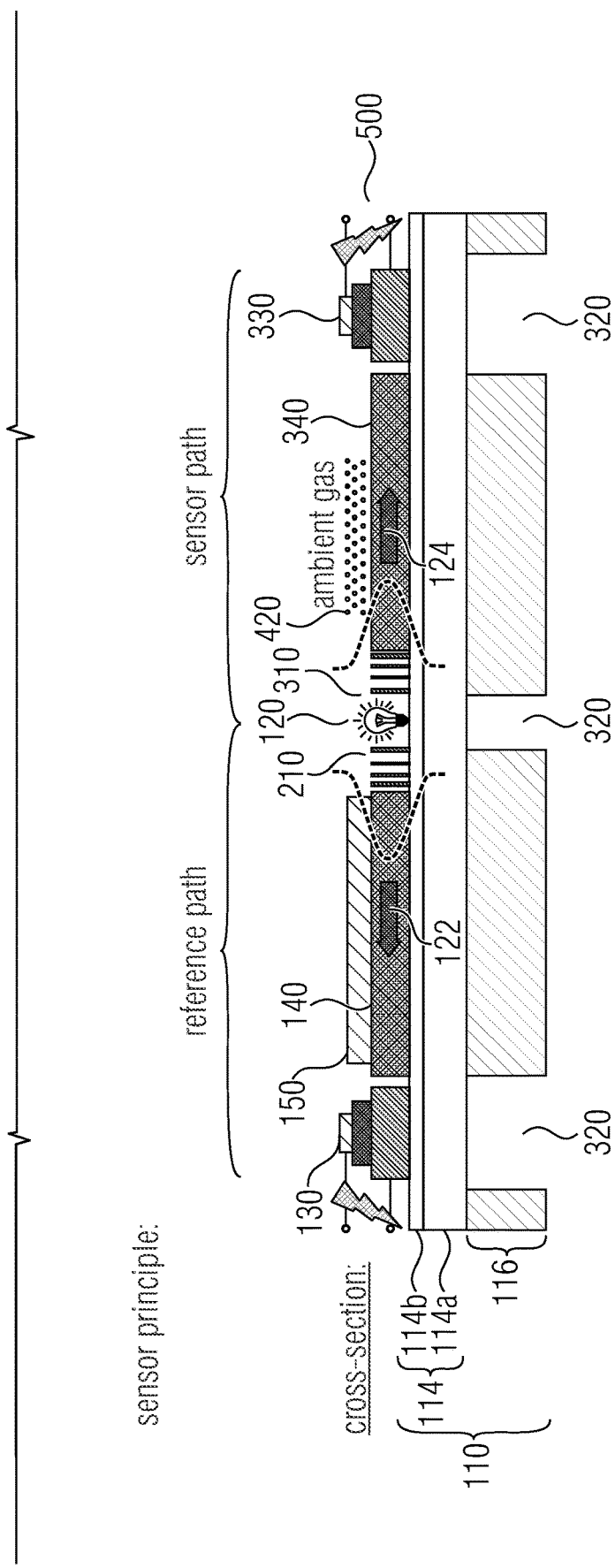
Fig. 5 (Part 2)

SENSOR AND METHOD FOR PERFORMING A REFERENCE MEASUREMENT WITH GUIDED THERMAL RADIATION

This application claims the benefit of European Patent Application No. 21177166, filed on Jun. 1, 2021, which application is hereby incorporated herein by reference.

TECHNICAL FIELD

Examples of the disclosure comprise sensors and methods for performing a reference measurement with guided thermal radiation.

BACKGROUND

For measuring individual gas concentrations in ambient air, signal evaluation is a challenge. One possibility is to compare the actual measurement with a reference measurement. In this manner, background noise may be more readily taken into account. Various requirements have to be met for a reference measurement to be able to be regarded as a reference. The reference measurement and the measurement itself must exhibit identical behavior with regard to changing external influences (e.g., a temperature change). In addition, influences such as fluctuations of the supply voltage must influence both measurements equally.

In order to overcome such challenges, there is a need for an improved concept for a reference measurement of a fluid sensor.

Such a need can be solved by the fluid sensor according to claim 1. Further, specific implementations of the fluid sensor are defined in the dependent claims.

SUMMARY

Examples of the disclosure comprise a fluid sensor for performing a reference measurement, the fluid sensor comprising a support structure having a top main surface region, wherein the top main surface region of the support structure forms a common system plane of the sensor. Furthermore, the fluid sensor comprises a thermal emitter on the top main surface region of the support structure, wherein the thermal emitter is configured to emit thermal radiation. The fluid sensor further comprises a first waveguide section on the top main surface region of the support structure and a first thermal radiation detector on the top main surface region of the support structure and a cover structure on at least one part of the first waveguide section, wherein the cover structure is configured to seal the at least one part of the first waveguide section. Moreover, the first waveguide section is configured to guide a first portion of the thermal radiation emitted by the thermal emitter to the first thermal radiation detector and the first thermal radiation detector is configured to detect the guided first portion of the thermal radiation for performing the reference measurement.

Further examples of the disclosure comprise a method for performing a reference measurement. The method comprises emitting thermal radiation by a thermal emitter, wherein the thermal emitter is arranged on a top main surface region of a support structure and wherein the top main surface region of the support structure forms a common system plane. The method further comprises guiding a first portion of the thermal radiation, emitted by the thermal emitter, to a first thermal radiation detector by a first waveguide section, wherein the first waveguide section and the first thermal radiation detector are arranged on the top main surface region of the support structure and wherein at least one part of the first waveguide section is sealed by a cover structure. In addition, the method comprises detecting the guided first portion of the thermal radiation for performing the reference measurement.

Examples of the disclosure are based on the idea to perform a reference measurement by guiding thermal radiation, emitted by a thermal emitter, via a first waveguide section, to a first thermal radiation detector. In order to suppress specific environmental impacts on the measurement, a cover structure is configured to seal at least one part of the first waveguide section. For example, an influence of an ambient fluid on the guided radiation, e.g. on an evanescence field of the guided radiation, guided by the first waveguide section, may be suppressed or reduced by physically blocking the fluid with the cover structure from the first waveguide section. Other environmental impacts, for example a temperature, may still affect the measurement.

Measurement of the guided radiation with reduced environment impacts may be used in order to determine an information about unsuppressed environmental effects, e.g. temperature or humidity, or an impact of said effects on the guided radiation that are not or only to a limited amount influenced by the cover structure. This information may be used to correct other measurements that are impacted by the environment in the same, or approximately same, manner as the reference measurement. For example, a fluid sensor may be configured to determine an information about a surrounding fluid. Simply measuring said fluid may lead to large measuring errors because of a dependency of the measurement on other environmental effects, e.g. temperature and humidity. Therefore, a reference measurement may be performed by suppressing an impact of the surrounding fluid to gain a reference of what the detector may measure without the fluid. Consequently, a second measurement, using a similar setup of emitter, waveguide section and detector but without cover, may be performed and its result may be corrected with the information of the reference measurement.

Moreover, not only environmental influences may be determined or compensated in that way. With the reference measurement, and for example an evaluation of a measurement trend over time, sensor parameters or a sensor condition, for example aging of the sensor and/or fluctuations of the supply voltage, may be determined or taken into account for a compensation or improvement of other measurements of the sensor. By reducing influences on the measurement via the cover structure, a reference measurement for monitoring may be implemented. Therefore, sensor gains and/or measurement characteristics may be adapted, in order to improve measurement precision. Adaptation may be performed in order to compensate influences of environmental effects, e.g. temperature, humidity, and/or effects such as a reduced sensitivity due to aging and/or sensor changes dependent of or according to the number of measurement cycles, e.g. especially for the emitter or heater.

In addition, usage of a waveguide allows to achieve an increased electrical efficiency. With a waveguide, a large amount of radiation emitted by the thermal emitter may be guided to the detector, e.g. a significantly larger amount in comparison to a concept without waveguide, because of thermal radiation losses of radiation being not oriented towards the detector. Moreover, usage of a waveguide allows for a well-defined transmission path between emitter and detector, which may therefore be easy to model. According to such a model, impacts of environmental effects may be corrected at a second measurement, e.g. for determination of characteristics of an ambient fluid.

Furthermore, usage of the waveguide section allows for a plurality of shapes of the transmission path between emitter and detector. Therefore, a fluid sensor according to the disclosure may be accommodated easily in circuits, even with limited, or oddly shaped spaces.

In simple words, examples according to the invention are based on the idea to use an encapsulated wave guide as reference path, e.g. for gas sensing applications.

BRIEF DESCRIPTION OF THE DRAWINGS

The drawings are not necessarily to scale, emphasis instead generally being placed upon illustrating the principles of the disclosure. In the following description, various examples of the disclosure are described with reference to the following drawings, in which:

FIG. 5 shows a schematic view of a fluid sensor, a schematic cross-section of the fluid sensor and a sensor principle of the fluid sensor according to examples of the disclosure;

DETAILED DESCRIPTION OF ILLUSTRATIVE EMBODIMENTS

Figure 1:
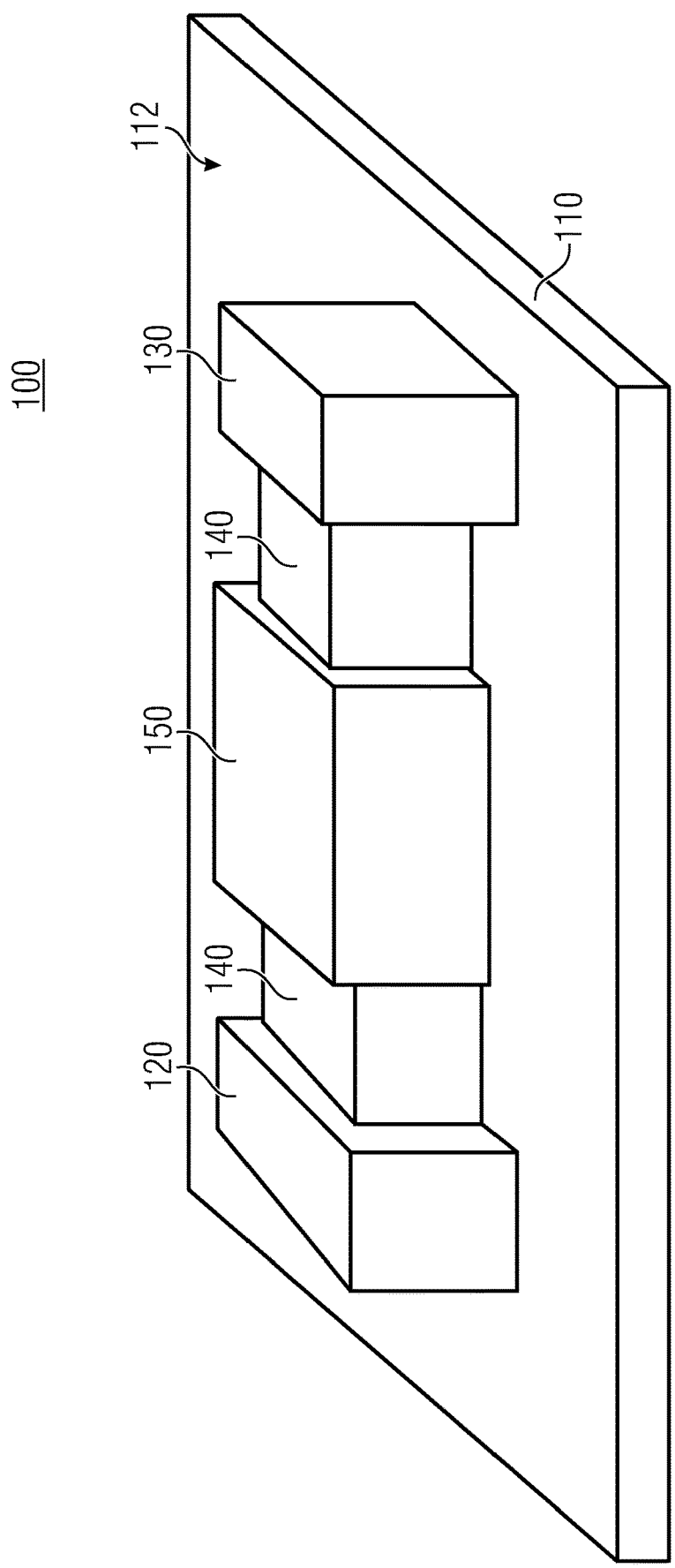
FIG. 1 shows a schematic view of a fluid sensor according to examples of the disclosure.

Equal or equivalent elements or elements with equal or equivalent functionality are denoted in the following description by equal or equivalent reference numerals even if occurring in different figures.

In the following description, a plurality of details is set forth to provide a more throughout explanation of examples of the present disclosure. However, it will be apparent to those skilled in the art that examples of the present disclosure may be practiced without these specific details. In other instances, well-known structures and devices are shown in block diagram form rather than in detail in order to avoid obscuring examples of the present disclosure. In addition, features of the different examples described herein after may be combined with each other, unless specifically noted otherwise.

FIG. 1 shows a schematic view of a fluid sensor according to examples of the disclosure. FIG. 1 shows fluid sensor wo comprising a support structure no having a top main surface region 112 and arranged on the top main surface region 112 a thermal emitter 120, a first thermal radiation detector 130 and in between the emitter 120 and the detector 130 a first waveguide section 140. Sensor 100 further comprises a cover structure 150, wherein the cover structure is arranged on the first waveguide section 140, sealing one part of the first waveguide section 140.

The thermal emitter 120 radiates thermal radiation, which is coupled into the first waveguide section 140. The first waveguide section 140 guides the thermal radiation to the first thermal radiation detector 130. One part of the first waveguide section 140 is sealed by the cover structure 150. Consequently, an ambient fluid (not shown) cannot or can only to a limited scope interact with the radiation, for example an evanescence field of the radiation, guided in the first waveguide structure 140. In general, the cover structure hinders certain environmental impacts, such as an influence of the ambient fluid, for example a gas, on the guided radiation. The radiation is then detected in the detector 130. By suppressing specific environmental effects, and by allowing other environmental effects to impact the guided thermal radiation, the detection of the guided thermal radiation by the detector 130 may provide a reference measurement.

In FIG. 1, the cover structure 150 is represented by an enclosure around a part of the first waveguide section 140. However, the cover structure 150 may have any form or shape suitable to hinder or block a specific environmental effect. In the example of a fluid sensor said impact to be blocked may be the fluid to be detected by a second measurement, in order to measure mainly or even only other environmental parameters, in order to correct the second measurement. In this case the cover structure may not hinder an impact of an environmental temperature on the guided radiation. On the other hand, in other applications, the cover structure may be configured to reduce an impact of a temperature by having isolating properties in order to determine other environmental effects.

The cover structure 150 may cover the whole first waveguide section 140 in order to suppress any damping from a specific environmental effect. However, by only covering a part of the first waveguide section 140 a defined damping may be implemented. For example, via a priori tests, a reference measurement with a defined damping may be used in order to correct a second measurement, e.g. the measurement to determine a characteristic of an ambient fluid.

According to further examples of the disclosure the fluid sensor 100 comprises a sealed cavity, and the sealed cavity is arranged between the cover structure 150 and at least one part of the first waveguide section 140. The cover structure 150 may be arranged directly on the first waveguide section 140 or with a gap or spacing in between the cover structure 150 and first waveguide section 140. In order to suppress specific environmental effects, the gap or spacing may be sealed, forming a sealed cavity. By being sealed, for example an ambient gas may not interact with the guided radiation, in the sealed part of the waveguide section 140, underneath the cover structure 150. An additional sealed cavity may increase a distance between an ambient fluid and the covered part of the first waveguide section 140, and therefore may reduce an influence of said fluid on the guided radiation.

According to further examples of the disclosure the sealed cavity comprises a defined atmosphere and/or a defined fluid, and the first waveguide section 140 is configured to enable an interaction of an evanescence field of the guided first portion of the thermal radiation with the defined atmosphere and/or the defined fluid in a predetermined way, such that the guided first portion of the thermal radiation comprises an information about the measuring conditions of the fluid sensor 100. The defined atmosphere may be a vacuum, at least in the technical sense, or a specific gas. The cavity may comprise or may be filled with a fluid. With a known, specific atmosphere or fluid, an impact of an environmental effect may be calculated based on the guided radiation detected by the first detector 130, for example because of an a priori determined information on the influence of said effects on guided radiation that interacts with the defined atmosphere and/or fluid. However, with such reference measurement, not only environmental effects may be compensated, but measurement impacts, such as aging of the sensor itself, may also be determined. In other words, the measuring conditions of the fluid sensor may comprise environmental parameters and/or impacts on a sensor measurement, as well as sensor parameters or sensor condition information. In simple words, a measurement principle of examples of the disclosure may be based on the idea of "defined gas" vs. "ambient gas", with a defined gas in the cavity providing an information, via an interaction with the first portion of the radiation, for correcting a measurement of an ambient gas.

According to further examples of the disclosure the fluid sensor 100 comprises a first filter structure and the first filter structure is configured to filter the first portion of the thermal radiation emitted by the thermal emitter 120. Furthermore, the first waveguide section 140 comprises the first filter structure, and/or the thermal emitter 120 comprises the first filter structure, and/or the first thermal radiation detector 130 comprises the first filter structure 140, and/or the first filter structure is arranged on the top main surface region 112 of the support structure no between the thermal emitter 120 and the first waveguide section 140 and/or between the first thermal radiation detector 130 and the first waveguide section 140.

In order to allow usage of the reference measurement in order to correct a second measurement, e.g. a second measurement with a second waveguide section without cover structure 150, to determine a characteristic of a fluid, both measurements should be performed as equally as possible, apart from the environmental impacts that are to be corrected. By filtering the thermal radiation, filtered thermal radiation may be provided in a spectrum with an evanescence field that is sensitive for a specific surrounding fluid to be detected, for example by the second measurement. Consequently, cheap thermal emitters 120 may be implemented, for example emitters 120 that emit a broadband thermal radiation, wherein the thermal radiation is, adapted, or put easy 'tuned' via the filtering for a specific application, for example the detection, or the determination of a concentration of a particular fluid. The fluid may, for example, be $CO_2$ and/or CO and/or any other gas or liquid. Consequently, radiation of the same spectrum may be used to perform the reference measurement to evaluate the environmental impact correctly or accurately or at least as accurately as possible.

According to further examples of the disclosure the thermal emitter 120 comprises a semiconductor strip; and the semiconductor strip is configured to emit a broadband thermal radiation, as the thermal radiation. Furthermore, the first filter structure is an optical filter structure comprising a semiconductor material and the optical filter structure has a narrow transmission band. Moreover, the optical filter structure is configured to filter the first portion of the broadband thermal radiation, emitted by the thermal emitter.

A semiconductor strip as a thermal emitter 120 is a cheap, and easy to fabricate semiconductor element. With a first waveguide section 140 according to examples of the disclosure, a fluid sensor 100 may be produced with low costs, but with a good efficiency, because of the harvesting and guiding of thermal radiation by the waveguide 140 from the emitter 120. A corresponding first optical filter structure may be produced with low cost and in large numbers as well, and may be configured to provide a narrow band thermal radiation, adapted to determine an information about a surrounding fluid or to provide the same narrow band thermal radiation for the reference measurement.

According to further examples of the disclosure the fluid sensor comprises a second waveguide section and a second thermal radiation detector, on the top main surface region 112 of the support structure 110. Furthermore, the second waveguide section is configured to guide a second portion of the thermal radiation, emitted by the thermal emitter 120, to the second thermal radiation detector; and the second waveguide section is configured to enable an interaction of an evanescence field of the guided second portion of the thermal radiation with a surrounding fluid. Moreover, the second thermal radiation detector is configured to detect the guided second portion of the thermal radiation, in order to determine an information about the surrounding fluid, based on the interaction of the evanescence field of the guided second portion of the thermal radiation and the surrounding fluid and based on the guided first portion of the thermal radiation, detected by the first thermal radiation detector 130.

With the second thermal radiation detector, the e.g. 'actual' fluid measurement, for example the before mentioned second measurement, for determining a characteristic of the surrounding fluid, may be performed. By placing the second waveguide and the second thermal radiation detector on the same support structure, both measurement paths may be impacted in the same way by environmental effects, e.g. temperature, apart from the influence, such as the influence of a fluid to be detected, in the part of the first waveguide section 140 that is covered and sealed by the cover structure 150. Therefore, together with the detection of the guided second portion of the thermal radiation, a determination of an information about the surrounding fluid may be determined and corrected, or in other words adjusted by subtracting or compensating the impact of (for the measurement of the fluid) unwanted environmental effects, being effects that are not or only to a limited scope hindered or suppressed by the cover structure 150, by evaluation of the first portion of thermal radiation, detected by the first thermal radiation detector 130. Consequently, an improved determination of an information or characteristic of the surrounding fluid may be provided.

According to further examples of the disclosure the fluid sensor comprises a second filter structure and the second filter structure is configured to filter the second portion of the thermal radiation emitted by the thermal emitter 120. Furthermore, the second waveguide section comprises the second filter structure and/or the thermal emitter 120 comprises the second filter structure, and/or the second thermal radiation detector comprises the second filter structure and/or the second filter structure is arranged on the top main surface region of the support structure no between the thermal emitter 120 and the second waveguide section and/or between the second thermal radiation detector and the second waveguide section.

As explained before, by filtering thermal radiation, filtered thermal radiation may be provided in a spectrum with an evanescence field that is sensitive for a specific surrounding fluid to be detected. The thermal radiation may be, adapted, or put easy 'tuned' via the filtering for a specific application, for example the detection, or the determination of a concentration of a particular fluid.

According to further examples of the disclosure the first and/or second waveguide section comprise at least one of a slab waveguide, a strip waveguide, a slot waveguide, a slot-array waveguide and a multi-slot waveguide and/or the first and/or second thermal radiation detector comprise at least one of a pyroelectric temperature sensor, a piezoelectric temperature sensor, a pn junction temperature sensor and a resistive temperature sensor.

Choice of waveguides according to a specific application may enable a high evanescence field ratio and therefore an improved fluid detection efficiency. The choice of the detector may be based on production costs and required detection accuracy.

According to further examples of the disclosure the thermal emitter 120 is configured to emit thermal radiation in at least two different radiation emission directions parallel to the system plane and a first and a second of the at least two different radiation emission directions are opposite to one another. Furthermore, the thermal emitter is configured to emit the first portion of the thermal radiation in the first radiation emission direction; and the thermal emitter is configured to emit the second portion of the thermal radiation in the second radiation emission direction.

With an emitter 120 emitting thermal radiation in two opposite thermal radiation directions, the first thermal radiation detector 130 may be arranged facing the first radiation direction, and the second thermal radiation detector may be arranged opposite to the first radiation detector 130, with the emitter 120 in between the two detectors, facing the second radiation direction. Such an arrangement may comprise a small lateral footprint, and therefore small production costs, because of the limited wafer space needed. However, the radiation emission directions may also comprise an arbitrary angle, for example, the arrangement of first detector 130, emitter 120 and second detector may have a triangular shape with the edges in between emitter 120 and first detector 130 and emitter 120 and second detector being the first and second thermal radiation emission directions. Anyways, it is to be noted that any arbitrary arrangement may be positioned, since the first and second waveguide sections may be configured to guide the radiation emitted by the emitter to wherever the first and/or second detector are placed.

According to further examples of the disclosure the first and/or second waveguide section are configured to provide an evanescent field ratio of the guided first and/or second portion of the thermal radiation of at least 5% and at most 90%. The evanescent field ratio may, for example be around 43%, for example at least 30% and at most 60%. However, according to examples of the disclosure the fluid sensor, and for example in particular the first and/or second waveguide sections, is/are configured to provide a high evanescent field ratio or in other words, an evanescent field ratio that is as high as possible, or 'as much as one can have'. One idea according to examples of the disclosure is to have the thermal radiation filtered to the correct wave length (small bandwidth), for example via the filter structure (first and/or second), and present as evanescent field in order to observe, for example as much as possible, damping by interaction with the surrounding fluid, for example an ambient gas, and to correct an evaluation of said observed interaction with the reference measurement, performed with the same radiation characteristics, e.g. evanescence field ratio. Furthermore, with regard to low evanescent field ratios, according to examples of the disclosure, the area, for example the footprint of the second waveguide section in the common system plane, and optionally the first waveguide section as well in order to equally compensate unwanted environmental impacts, may be increased or may be maximized or may be large, in order to compensate the effect of a small evanescent field on the determination of the surrounding fluid. On the other hand, the first and/or second waveguide section may be configured to provide an evanescent field ratio of the guided first and/or second portion of the thermal radiation of at most 90%.

According to further examples of the disclosure, the first and/or second waveguide sections may be configured to provide low evanescent field ratios. Such an arrangement may, for example, be producible with lower costs. Such examples of the disclosure may be used for low-cost applications. However, a loss in accuracy because of the low evanescent field ratio may be compensated or even over compensated or at least mitigated by the reference measurement. By performing the reference measurement and by increasing the accuracy of the measurement of the second detector based thereof, a good estimation of a characteristic of an ambient fluid may be performed.

According to further embodiments of the invention first and second waveguide sections may be configured to provide different evanescent field ratios. The second waveguide section may, for example, be configured to provide a high evanescent field ratio, in order to enable a strong interaction of the radiation with the ambient gas. On the other hand, the first waveguide section may, for example, be configured to provide a lower evanescent field ratio. Even though measurements in the first and second detector may not be performed under equal conditions, e.g. equal evanescent field ratios, an improvement of the accuracy of a determination of a characteristic of an ambient fluid may still be performed based on the reference measurement.

In other words, the waveguide, e.g. the first waveguide section, for the reference, e.g. the reference measurement, could also deal with low values of evanescent field ratio; it may make no difference whether one would have a reference measurement with high evanescent field of a defined gas or with a low evanescent field ratio; Concerning the evanescent field ratio "as much as one can have" may, for example, be especially true for the actual measurement waveguide path, e.g. the second waveguide section, but not necessarily for the reference path. According to examples of the disclosure, the same wave guide, e.g. for the first and second waveguide section, may be used and only one part for referencing may be covered, but this is not a must. For example, a slab wave guide may be easier to be covered and according to examples, a multi-slot wave guide for the measurement and a slab waveguide for referencing, which is covered or encapsulated, may be combined, for example resulting in different evanescent field ratios for the first and second waveguide section.

As another example, the second waveguide section, e.g. comprising a multi-slot waveguide, may be configured to provide an evanescence field ratio of above 20%, e.g. in order to provide a conclusive measurement, wherein the first waveguide section, e.g. comprising a slab waveguide, may be configured to provide a lower evanescence field ratio, e.g. a field ratio of above 5%. For example, in simple words, sensing, e.g. an ambient fluid with unknown characteristics, based on the evanescent field may make sense above 20%, e.g. with an evanescence field ratio above 20%; the reference path could also deal with a lower evanescent field ratio wave guide, for example a slab wave guide with only 5% evanescent field ratio or an evanescent filed ratio of at least 5%. Therefore, for example, the reference path may be configured to be covered easily in order to provide the reference measurement path.

According to further examples of the disclosure the support structure 110 comprises a rigid structure and a substrate on a bottom surface of the rigid structure and a top surface, opposite to the bottom surface, of the rigid structure is the top main surface region. In addition, the rigid structure is configured to confine the thermal radiation, radiated by the thermal emitter.

On goal of the arrangement of the fluid sensor is, for example, to guide as much thermal radiation, radiated by the thermal emitter 120, to the second thermal radiation detector, wherein, in between the two, an evanescent field of the guided thermal radiation interacts with a surrounding fluid in order to determine an information about the fluid. Consequently, in order to compensate unwanted environmental effects, such as an ambient temperature dependency, the same goes for thermal emitter 120 and the first thermal radiation detector 130. Therefore, the rigid structure is configured to confine the thermal radiation, such that the thermal radiation does not leak through the support structure 110 or is absorbed by it. Therefore, according to examples of the disclosure rigid structures may be implemented, having mirror like properties. In some cases, it may be best, if the rigid structure would act like a mirror for the radiation guided through the first and/or second waveguide section. Consequently, the rigid structure may be configured to have a particular, for example 'correct' thickness and may be made of a particular, for example 'correct' materials, e.g. in order to fulfill this task. Additionally, or alternatively, two aspects may be fulfilled by the rigid structure:

1) The rigid structure may be configured, such that the exponential decay of the electric field guided through the first and/or second waveguide section may happen inside the rigid structure. Therefore, there may be only minor or for example even no contact to the substrate.

2) As the top of rigid structure builds an interface to the bottom of the first and/or second waveguide section, a wrong choice of material (or material thickness) may increase losses of the first and/or second waveguide section. Therefore, the rigid structure may be made of materials, or of materials with a certain thickness, configured to decrease waveguide losses.

The support structure or the rigid structure of the support structure no may comprise or even be made of Nitride and $SiO_2$. However, these materials may be varied according to a specific application, in other words this may be a specific combination of materials.

The $SiO_2$ may act as etch stop layer for a backside cavity etch, e.g. a substrate cavity etch, and may decouple the sensor from the substrate (e.g., thermally and leakage current). The Nitride may provide or give, for example, some strength to the membrane (The addition of the Nitride may enable providing a good membrane in combination with the $SiO_2$) and may act as a layer that contributes low losses to the first and/or second waveguide section. The situation for or for example performance of the emitter 120, e.g. heater and/or first and/or second detector may be improved if the $SiO_2$ is etched away after backside etching in order to end up with a membrane formed just by Nitride.

In general, examples of the disclosure are not limited to specific materials that are underneath the first and/or second waveguide or to certain layers that used to form the membranes. According to examples of the disclosure materials may be applied that are configured to decrease or to help to decrease the membrane thickness and introduce low losses to the waveguides.

According to one aspect of an example of the disclosure Nitride and $SiO_2$ may be suitable, but a man skilled in the art can potentially define other layer compositions which keeps the sensor system the same or equivalent without leaving the scope of this disclosure.

According to further examples of the disclosure the substrate comprises at least one substrate cavity; and the at least one substrate cavity is arranged vertically, with respect to the system plane, below the thermal emitter 120 and/or the first and/or the second thermal radiation detector and/or the first and/or second waveguide section, for thermal insulation, of the thermal emitter 120 and/or the first and/or the second thermal radiation detector and/or the first and/or second waveguide section, from the substrate. The cavities may be etched in the substrate. Therefore, adding cavities to the fluid sensor may be a cheap possibility to increase electrical efficiency because of less thermal radiation losses to the substrate.

According to further examples of the disclosure the fluid sensor has a footprint in the system plane of less than 45 $mm^2$ of less than 30 $mm^2$ or less than 25 $mm^2$ or less than 15 $mm^2$ and/or a height, wherein the height is orthogonal to the system plane, of less than 1000 μm or less than 950 μm or less than 800 μm. Decreasing the thickness of the fluid sensor may increase the amount of chips on the wafer as an inter-chip-spacing could be reduced. Therefore, the fluid sensor may be produced with reduced costs. With decreased length, more fluid sensors may be arrangeable on a single wafer, lowering the production costs.

According to further examples of the disclosure at least one of the first and/or the second thermal radiation detector, the first and/or the second waveguide section, the first and/or the second filter structure and/or the thermal emitter is arranged monolithically on the support structure. A monolithic fabrication allows for small dimensions of the fluid sensor 100, therefore saving space on a wafer and consequently costs. Furthermore, deposition processes may be used in order to produce such an arrangement. Such processes may be performed with low cost, and for high volume production.

Figure 2:
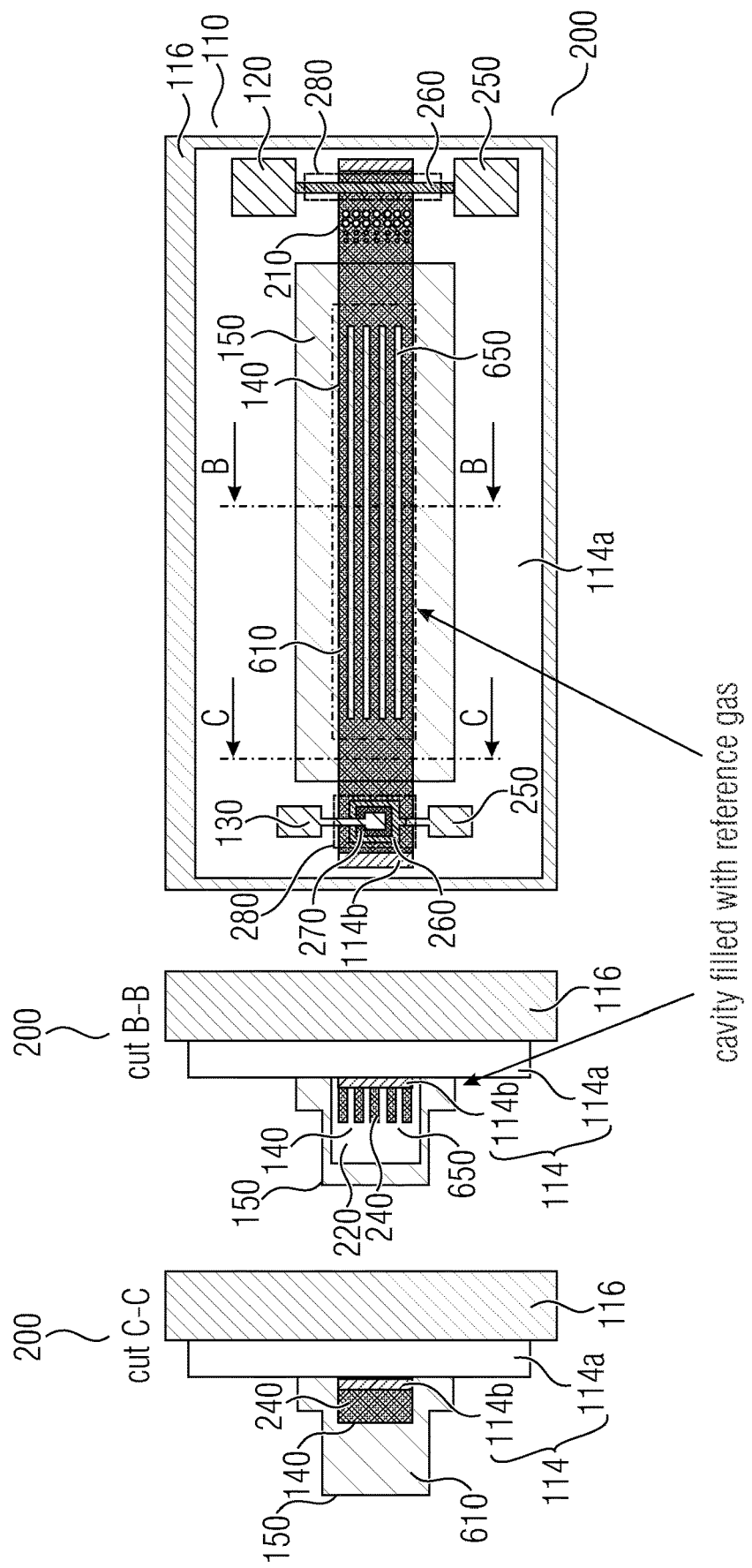
FIG. 2 shows a schematic view of a fluid sensor with a sealed cavity according to examples of the disclosure.

FIG. 2 shows a schematic view of a fluid sensor with a sealed cavity according to examples of the disclosure. FIG. 2 may show details for a reference path of a fluid sensor according to examples of the disclosure with multi-slot waveguides. FIG. 2 shows, on the right-hand side, a schematic top view of a fluid sensor 200 comprising a support structure no having a top main surface region and arranged on the top main surface region a thermal emitter 120, a first thermal radiation detector 130 and in between the emitter 120 and the detector 130 a first waveguide section 140. Sensor 200 further comprises a cover structure 150, wherein the cover structure is arranged on the first waveguide section 140, sealing one part of the first waveguide section 140. The cover structure 150 may be a bonded (Glass-) Cover. Therefore, examples of the disclosure may comprise (e.g., for producing a fluid sensor according to examples of the disclosure) or even require bonding processes, e.g. such as anodic bonding, glass frit bonding, eutectic bonding, etc.

Fluid sensor 200 further comprises a first filter structure 210. First filter structure 210 is arranged between emitter 120 and first waveguide section 140. However, it is to be noted that the first waveguide section 140 may comprise the first filter structure 210, and/or that the thermal emitter 120 may comprise the first filter structure 210, and/or that the first thermal radiation detector 130 may comprise the first filter structure 210, and/or that the first filter structure 210 may be arranged on the top main surface region of the support structure no between the thermal emitter 120 and the first waveguide section 140 and/or between the first thermal radiation detector 130 and the first waveguide section 140. The filter structure 210 may be arranged at any suitable position in the fluid sensor 200. The filter structure 210 may comprise etched holes in order to provide filtering characteristics.

By filtering, radiation may be provided having a wavelength, or a wavelength interval, that may be guided by a second waveguide, such that an evanescence field of the guided radiation with the specific wavelength may interact with a fluid to be determined. Accordingly, as shown in FIG. 2, in order to provide a meaningful reference measurement, the same filtering may be applied to the first portion of the radiation guided by the first waveguide section 140, in order to be influenced equally by environmental effects, or for example by sensor properties that may change over time, in order to compensate said effects or properties for the measurement of the fluid, e.g., the before mentioned second measurement.

As an optional feature the support structure no comprises a substrate 116 and a rigid structure 114, the rigid structure comprising optionally a first layer comprising $SiO_2$ 114a and second layer comprising Nitride 114b. The substrate 116 is arranged on a bottom surface of the rigid structure 114, wherein a top surface, opposite of the bottom surface, of the rigid structure is the top main surface region. The rigid structure 114 is configured to confine the thermal radiation, radiated by the thermal emitter 120. In other words, the rigid structure 114 is configured to provide a heat shield in order to keep the radiation from being absorbed by the substrate 116 and therefore to improve efficiency of the sensor 200. In simple words, the rigid structure 114 may keep the radiation or at least a significant amount of radiation above the substrate and in the first waveguide section 140 and in the first detector 130 and the rigid structure 114 may suppress a radiation direction of the emitter oriented in the substrate 116.

FIG. 2 shows, on the left-hand side, schematic side view of two cuts along the indicated sections of fluid sensor 200. As shown in the side view of section B-B, the sensor wo comprises a sealed cavity 220 between the cover structure 150 and one part of the first waveguide section 140.

As an optional feature, the cavity may be, as indicated in FIG. 2, filled with a reference gas. In general, such a cavity may comprise a defined atmosphere, for example a gas with a specific concentration having a specific pressure, and/or a fluid, for example a liquid or a liquid and a gas. The gas or fluid may be configured to interact with an evanescence field of the radiation guided in the first waveguide section 140, such that an information about an environmental impact, or environmental parameter may be determined. The gas or fluid may be chosen in a way that its interaction with the guided radiation may be highly sensitive towards a particular, or several environmental parameters, e.g., a change in temperature. Therefore, by detecting the first portion of the radiation in the first thermal radiation detector 130 an information may be determined which may be used in order to correct a second measurement, which is also affected by the environmental parameter. As explained before, measuring conditions of the sensor may be determined with the reference measurement, the measuring conditions not only comprising environmental conditions, but, for example also hardware information about the sensor itself, for example an impact of aging.

As another optional feature, the first waveguide section 140 comprises a multi-slot waveguide 650.

The second section C-C through sensor 200 shows a portion of the first waveguide section 140 without a cavity. As shown, the waveguide section 140 may comprise a slab waveguide 610. As another optional feature, as shown, the slab and/or the slots of the waveguides may comprise Poly-Si 240 (Poly-Silicon). In proximity to transitions from waveguide to emitter or detector a simpler geometry of the waveguide may be implemented for easier fabrication or improved radiation coupling.

As shown in FIG. 2, the emitter 120 and the first detector 130 may comprise support and/or contact portions 250, which may comprise AlSiCu. As shown, the emitter 120 may optionally comprise a semiconductor strip, which may comprise doped Poly-Si 260. The first detector 130 may optionally comprise, e.g., in an area of the detector configured to detect thermal radiation, a radiation absorption layer, e.g. comprising doped Poly-Si 260, and in addition a detection layer, e.g., a piezo layer comprising an AlN/AlScN material 270. In addition, the first detector 130 may comprise, as shown, in between the support and/or contact portions 250 another area being made of the same material as support and/or contact portions 250, e.g., AlSiCu, for example for contacting support and/or contact portions 250 with the area of the detector 130 that is configured to detect thermal radiation, in order to provide an electrical signal. In general, the first detector 130 may be a piezoelectric temperature sensor. The respective support and/or contact portions 250 may be used for contacting, e.g., for providing a current for heating the semiconductor strip for the emitter 120 and/or for detecting a voltage induced by the heating of the doped poly-Si 260 of the detector 130. However, the fluid sensor 200 is neither limited to a specific filter 210, nor to the specific materials used. In addition, the heater 120, the WG(s) 140, the filter 210, and the detector 130 may form sub-systems of the fluid sensor 200.

The emitter may optionally be configured, for example with the semiconductor strip, to emit a broadband thermal radiation. Therefore, the emitting portion of the emitter, e.g., the semiconductor strip that may comprise Poly-Si 260, e.g. a strip of Poly-Si (poly silicon) with an implantation, may be producible with low costs and in a simple way. Optionally, according to examples of the disclosure, the semiconductor strip may, for example be replaced by a metal strip, e.g. at some point once the for example reliability of the sensor makes it necessary. For example, for applications that require a high reliability of the sensor, emitters according to examples of the disclosure may comprise a metal strip that is heated via an electric current in order to provide the thermal radiation. In order to provide radiation around a wavelength that may be beneficial for an interaction with a fluid to be detected, the first filter structure 210 may be an optical filter structure comprising a semiconductor material, and having a narrow transmission band. For example, in case a filter structure is arranged in between a detector and a waveguide section for a second measurement path for a determination of an ambient fluid, the filter may suppress radiation having interacted, or to be more specific radiation of which an evanescence field has interacted, with one or more fluids that may not be of interest for the measurement. Respectively, as shown, in order to provide a reference measurement an equivalent setup may be arranged in between emitter 120, first waveguide section 140 and first detector 130.

The dashed lines around the semiconductor strip of the emitter 120 and the area of the first detector 130 indicate the optional use of a backside Bosch Process 280, in order to produce the before mentioned elements. However, this process is only optional, and therefore fluid sensors as shown in FIGS. 1 and 2 may be fabricated in any suitable manner. For example, other deep reactive-ion etching processes or modifications thereof may be used in order fabricate the emitter 120 and/or the first detector 130. In general, according to examples of the disclosure, emitter 120 and/or first detector 130 may comprise a geometry with steep-sided trenches, fabricated via etching. Therefore, emitter 120 and first detector 130 may comprise high aspect ratios.

Figure 3:
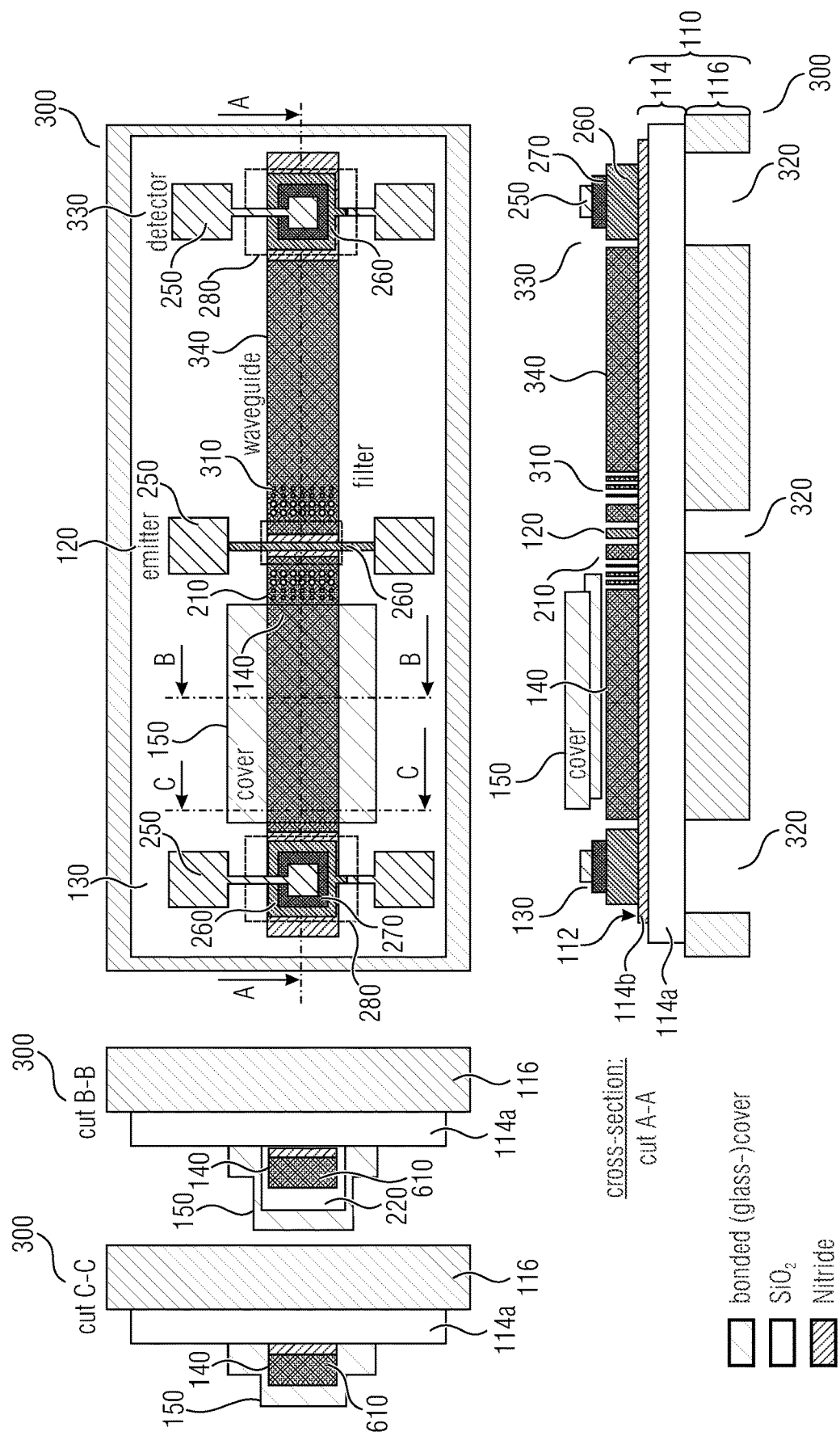
FIG. 3 shows a schematic view of a fluid sensor having a second waveguide section and detector according to examples of the disclosure.

FIG. 3 shows a schematic view of a fluid sensor having a second waveguide section and detector according to examples of the disclosure. Fluid sensor 300 shown in FIG. 3 may be an integrated sensor system. FIG. 3 shows a schematic top view and schematic cuts through sections C-C and B-B analogously to FIG. 2. In addition, FIG. 3 shows a Cross-Section Cut through section A-A below the schematic top view. Apart from elements already explained in the context of FIG. 1 and FIG. 2, fluid sensor 300 comprises a second filter structure 310, a second waveguide section 340 and a second thermal radiation detector 330. In addition, the top main surface region 112 of support structure no is shown. The second filter structure 310 and the second thermal radiation detector 330 may be structured and/or may provide functionality according to the first filter structure 210 and the first thermal radiation detector 130 or according to any of the aspects explained above. Therefore, explanations in the context of the first filter structure 210 and the first thermal radiation detector 130 may be applied analogously to the second filter structure 310 and the second thermal radiation detector 330. A difference may be the use of the second filter structure 310 and the second thermal radiation detector 330 in order to determine an information about a surrounding fluid and the use of the first filter structure 210 and the first thermal radiation detector 130 in order to determine a reference measurement in order to correct the information about the surrounding fluid.

The second waveguide section 340 may guide a second portion of the thermal radiation, radiated by thermal emitter 120 to the second thermal radiation detector 330. An evanescence field of the second portion of the guided radiation may interact with a surrounding fluid. By detecting the guided second portion of the thermal radiation, an information about the surrounding fluid may be determined. However, because of environmental effects, e.g., an unknown impact of an ambient temperature, the information determinable by the measurement of the second detector 330 may not be precise. Therefore, a first portion of the thermal radiation emitted by the emitter 120, as explained before, may be guided by the first waveguide section 140 to the first detector 130. Because of the covering structure 150, an interaction of the guided first portion of the thermal radiation with the ambient fluid may be suppressed or hindered. Therefore, the measurement provided by the first detector 130 may be used in order to correct or compensate the information about the surrounding fluid.

In FIG. 3, as shown, optionally the second filter structure 310 is arranged between second detector 330 and second waveguide section 340. However, in general, the second waveguide section 340 may comprise the second filter structure, and/or the thermal emitter 120 may comprise the second filter structure 310, and/or the second thermal radiation detector 330 may comprise the second filter structure 310, and/or the second filter structure 310 is arranged on the top main surface region of the support structure no between the thermal emitter 120 and the second waveguide section 340 and/or between the second thermal radiation detector 330 and the second waveguide section 340.

In contrast to fluid sensor 200, fluid sensor 300 comprises, as shown in section B-B in the part of the first waveguide section 140 that is sealed by the cover structure 150 a slab waveguide 610. The first waveguide section 140, as well as the second waveguide section 340 may comprise any form of waveguide suitable or a combination thereof. Further examples for waveguides will be presented with FIG. 6.

As another optional feature, as shown in FIG. 3 the thermal emitter 120 is configured to emit thermal radiation in two different radiation emission directions a first one being towards the first detector 130 and a second one being towards the second detector 330. In this example, the first and a second radiation emission directions are opposite to one another. Consequently, the first portion of thermal emission is coupled into the first waveguide section 140 and the second portion of thermal emission is coupled into the second waveguide section 340.

As shown in the cross-section through Cut A-A below the top view of sensor 300, sensor 300 may comprise substrate cavities 320. Optionally, as shown, substrate cavities 320 may be arranged vertically, with respect to the system plane, below the thermal emitter 120 and/or the first and/or the second thermal radiation detector 130, 330 and/or the first and/or second waveguide section 140, 340 (not shown), for thermal insulation and/or thermal isolation, of the thermal emitter 120 and/or the first and/or the second thermal radiation detector 130, 330 and/or the first and/or second waveguide section 140, 340, from the substrate 116.

In other words, a sensor system or integrated sensor system, e.g. fluid sensor according to examples of the disclosure comprises or employs, e.g. used as a basis a thermal emitter 120 (e.g., comprising a wavelength filter 210, 310), a waveguide (WG, e.g. a first and/or second waveguide section 140, 340) and a first and/or second detector 130, 330, e.g. a pyrodetector (e.g., temperature-sensitive diode, piezodetector). An interaction between the routed or guided radiation and an ambient fluid, e.g., the ambient air may occur along the WG. Radiation having a suitable wavelength (e.g., via narrow-band wavelength filtering) may be used for reaffirming, e.g., the presence of $CO_2$ in the ambient air, or to determine the concentration, e.g., by means of spectroscopy.

For implementing the reference path, an emitter 120 may be coupled into two WGs, e.g. the first and second waveguide section 140, 340 and may be evaluated on two detectors, e.g. the first and second detector 130, 330. One of these paths may serve measurement, the second path may represent the reference. To this end, it may be beneficial or even necessary to suppress any interaction with the ambient air on the reference path. One challenge consists in finding a suitable "cover" for the WG. Examples according to the disclosure solve this problem with the before mentioned arrangements of fluid sensors 100, 200, 300 and for example in particular with cover structure 150.

In the context of FIG. 3, sensor 200 of FIG. 2 may be a detailed schematic view of the reference path with multi-slot waveguides.

Figure 4:
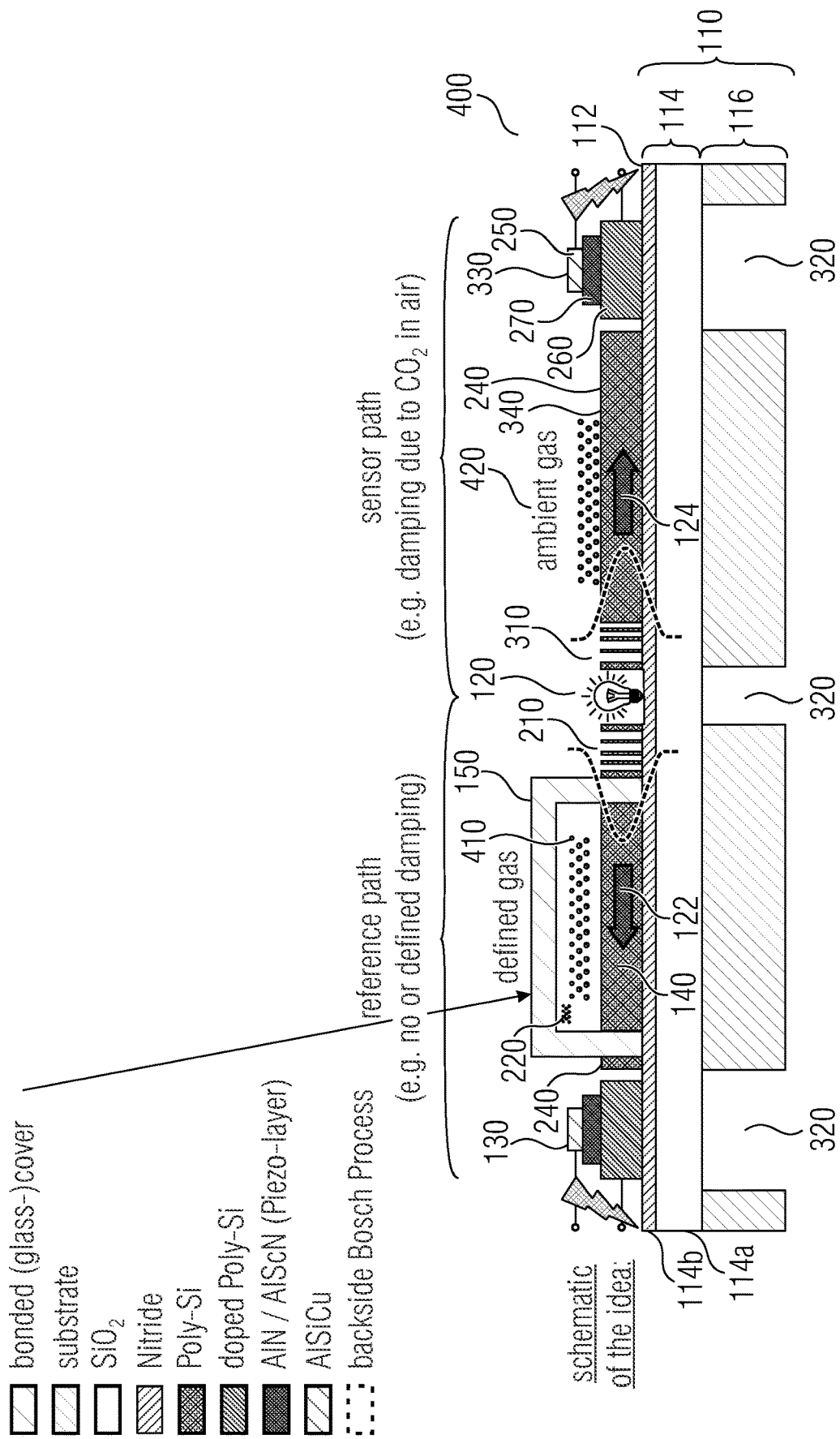
FIG. 4 shows a schematic sideview of a fluid sensor with a cavity with a defined gas according to an example of the disclosure.

FIG. 4 shows a schematic sideview of a fluid sensor according to an example of the disclosure. FIG. 4 shows a schematic of the idea or the sensor principle of a fluid sensor 500, which may be an integrated sensor system according to examples of the disclosure. Apart from elements already explained in the context of FIGS. 1, 2 and 3, in FIG. 4 first and second radiation emission directions 122, 124 of sensor 500 are shown. In addition, cavity 220 of sensor 500 between the cover structure 150 and the first waveguide section 140 comprises a defined gas 410, for example a reference gas, which may be configured to be sensitive to an environmental effect. For example, an evanescence field of the first portion of the thermal radiation emitted by the emitter 120 may interact with the defined gas, such that the first detector 130 may determine an information about the environmental effect. Equally, the gas may be sensitive to a measurement condition of the sensor, an interaction with the evanescence field may vary due to aging. With the information collected a measurement of a characteristic of an ambient gas 420 may be determined with detector 330.

In other words, the radiation path from emitter 120 to first detector 130 via the first waveguide section 140 may form a reference path, for example with no or a defined damping, for example of the first portion of radiation. On the other hand, a radiation path from emitter 120, to second detector 330 via the second waveguide section 340 may form a sensor path, for example with a damping of the second portion of radiation because of the ambient gas, e.g. $CO_2$.

FIG. 5 shows a schematic view of a fluid sensor, a schematic cross-section of the fluid sensor and a sensor principle of the fluid sensor according to examples of the disclosure. As shown in the schematic top view of fluid sensor 500, apart from elements already explained in the context of FIGS. 1, 2, 3, 5, and FIG. 5, the senor may comprise a length in a first lateral direction of less than 5 mm and a width in a second lateral direction of less than 3 mm. As shown in the corresponding cross-section below, a height of the sensor 500, perpendicular to the top surface region 112 may be less than 450 μm.

In addition, least one of the first and/or the second thermal radiation detector 130, 330, the first and/or the second waveguide section 140, 340, the first and/or the second filter structure 210, 310 and the thermal emitter 120 may be arranged monolithically on the support structure.

Furthermore, fluid sensor 500 may have a footprint in the system plane of less than 45 mm² of less than 30 mm² or less than 25 mm² and/or a height, wherein the height is orthogonal to the system plane, of less than 1000 μm or less than 950 μm or less than 800 μm.

The monolithic structure of the fluid sensor may enable a low height, resulting in small devices. In addition, an arrangement as shown in FIG. 5 may comprise synergistic effects because of an increased emitter efficiency by using radiation emitted in different radiation directions, by improving efficiency by using waveguides and by minimizing the footprint with a symmetrical setup of first and second detector around the emitter. However, a triangular setup may also be possible. In general, by using waveguides any form or shape appropriate for a specific application may be formed by fluid sensor 500.

In addition, FIG. 5 shows an example of the sensor principle of fluid sensor 500 in the cross-section of fluid sensor 500 on the bottom. This is in accord with the principle of fluid sensor 400 of FIG. 4 apart from sensor 500 not comprising a cavity between cover structure 150 and first waveguide section 140 and therefore not comprising a reference gas, or fluid, or a defined atmosphere.

Figure 6:
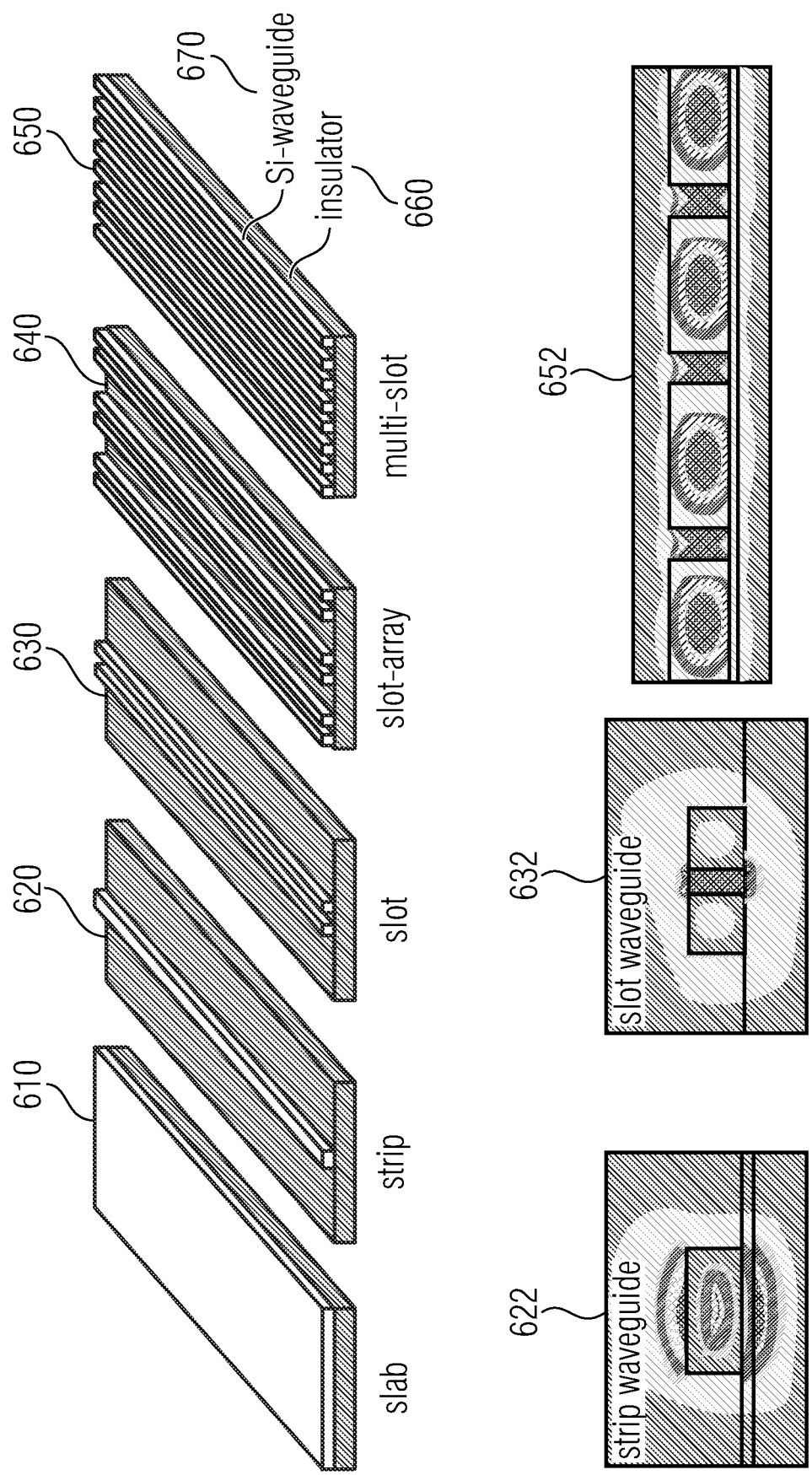
FIG. 6 shows a schematic view of possible implementations of the first and/or second waveguide section according to examples of the disclosure.

FIG. 6 shows a schematic view of possible implementations of the first and/or second waveguide section 140, 340 according to examples of the disclosure. FIG. 6 shows from left to right a slab waveguide 610, a strip waveguide 620, a slot waveguide 630, a slot-array waveguide 640 and a multi-slot waveguide 650. As an example, the waveguides may comprise an insulator 660 on which the slab, the strips and/or the slots are arranged comprising Si 670. In other words, the waveguides may be Si-waveguides. As an example, FIG. 6 shows schematic electric field distributions 622, 632, 652 of an evanescent field of thermal radiation for a strip waveguide (622), for a slot waveguide (632) and for a multi-slot waveguide (652). The colors represent the respective values of the field strength, with red being a high value, and blue being a low value.

As an example, a multi-slot waveguide 650 may provide an evanescent field ration of ~40%, with a damping of ~2-4 $cm^{-1}$. However, other evanescent field ratios may be implemented. For example, the first and/or second waveguide section 140, 340 may be configured to provide an evanescent field ratio of the guided first and/or second portion of the thermal radiation of at least 5% and at most 90%. Although increasing the evanescent field ratio may be improving the electric efficiency of the fluid sensor, in some cases it may not be possible to use a waveguide providing a high ratio. Therefore, according to examples of the disclosure an area of the first and/or second waveguide section 140, 340 may be increased in order to allow for a sufficient interaction between evanescent field of the guided radiation and surrounding fluid 420, for example in order to determine an information about the surrounding fluid. However, both effects may be used to provide a highly efficient fluid sensor, having a first and/or second waveguide structure 140, 340 with a large evanescence field ratio and a large area that is in contact with a surrounding fluid 420 or providing a reference measurement respectively.

Figure 7:
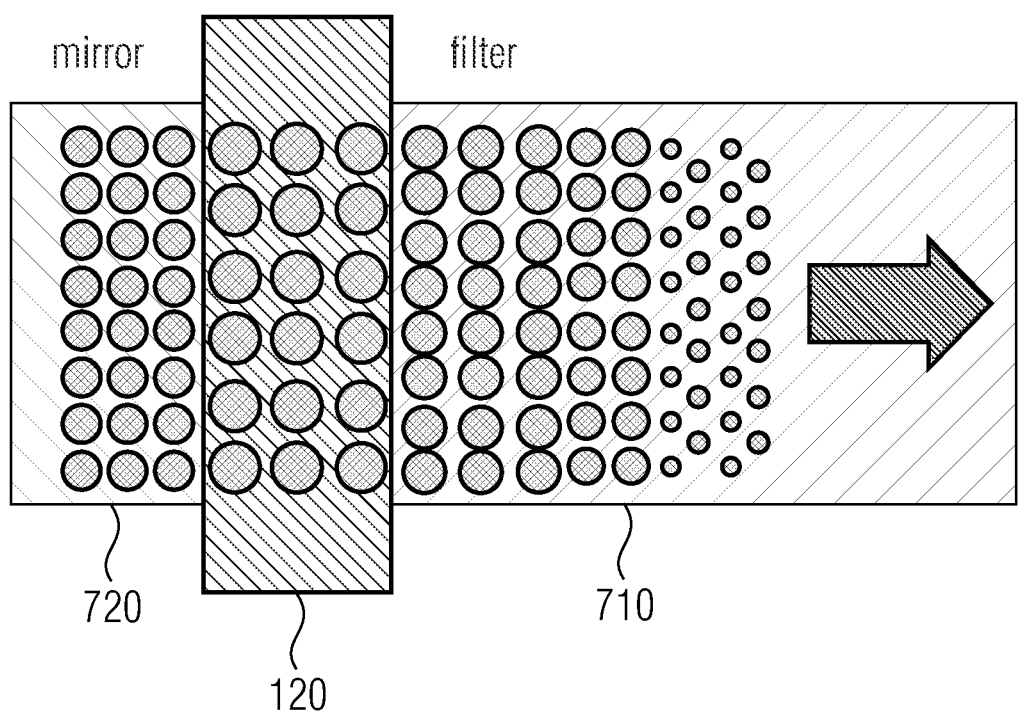
FIG. 7 shows a schematic view of a photonic crystal emitter as an example of a combination of a thermal emitter and a filter structure according to an example of the disclosure.

FIG. 7 shows a schematic view of a photonic crystal emitter as an example of a combination of a thermal emitter and a filter structure according to an example of the disclosure. Photonic crystal emitter 700 comprises a thermal emitter 120 and a filter structure 710. Therefore, the photonic crystal emitter 700 may be configured to emit filtered radiation. The thermal emitter 120 may be an implanted strip through which a current may flow, therefore this particular strip may get hot and emit the radiation. Therefore, the thermal emitter 120 may be the driven and/or intentional heated/emitting part of the photonic crystal thermal emitter. The filter structure 710 may be the first and/or second filter structure 210, 310. As an optional feature, for example in order to focus radiation in one direction, e.g. in a first radiation emission direction of a plurality of radiation emission directions, photonic crystal emitter 700 optionally comprises a mirror 720. Mirror 720 may increase the efficiency of the emitter. As an example, e.g. for a better understanding, if one thinks of a mirror part 720 that has some distance to the implanted area 120 and a filter 710 that also has some distance, e.g. to the implanted area and/or the mirror, that it would be clear separated, or for example then the photonic crystal emitter 700 may be clearly separated, into photonic crystal mirror 720, thermal emitter 120 and photonic crystal filter 710. As an example, the photonic crystal emitter 700, e.g. photonic crystal thermal emitter may comprise a thermal emitter 120 in the form of an implanted area or implanted strip, a photonic crystal filter 710 and optionally a photonic crystal mirror 720.

An arrangement as explained before may be implemented with a thermal emitter 120 having two or more radiation emission directions, wherein the radiation emission direction shown in FIG. 7 is a first radiation emission direction, which is not opposite to one of the other radiation emission directions in the same plane. A setup with mirrors may be implemented for a three-dimensional setup, with radiation directions, that are not parallel to the system plane. However, a second radiation emission direction may be directed in the system plane, but not opposite for shown first radiation emission direction, e.g. with an angle in the system plane of 90°. However, for the sake of convenience only one radiation emission direction (indicated with an arrow) is shown in FIG. 7. On the other hand, photonic crystal emitter 700 may be used as emitter 120 of fluid sensor 200 of FIG. 2 having only one radiation emission direction towards a first detector 130. Consequently, the mirror 710 may improve electrical efficiency. The phonic crystal emitter 700 comprises etched holes for filtering and to provide the mirror characteristics. Input power of the photonic crystal emitter may be ~100 mW (for example having a length of 500 μm, and at @~750K). A band width of radiated emission may be ~800 nm.

In addition or alternatively to comprising a phonic crystal structure, for example as shown in FIG. 7, the filter structure 710, e.g. the first and/or section filter structure 210, 310, may comprise a Bragg filter structure as a wavelength selective optical element.

Figure 8:
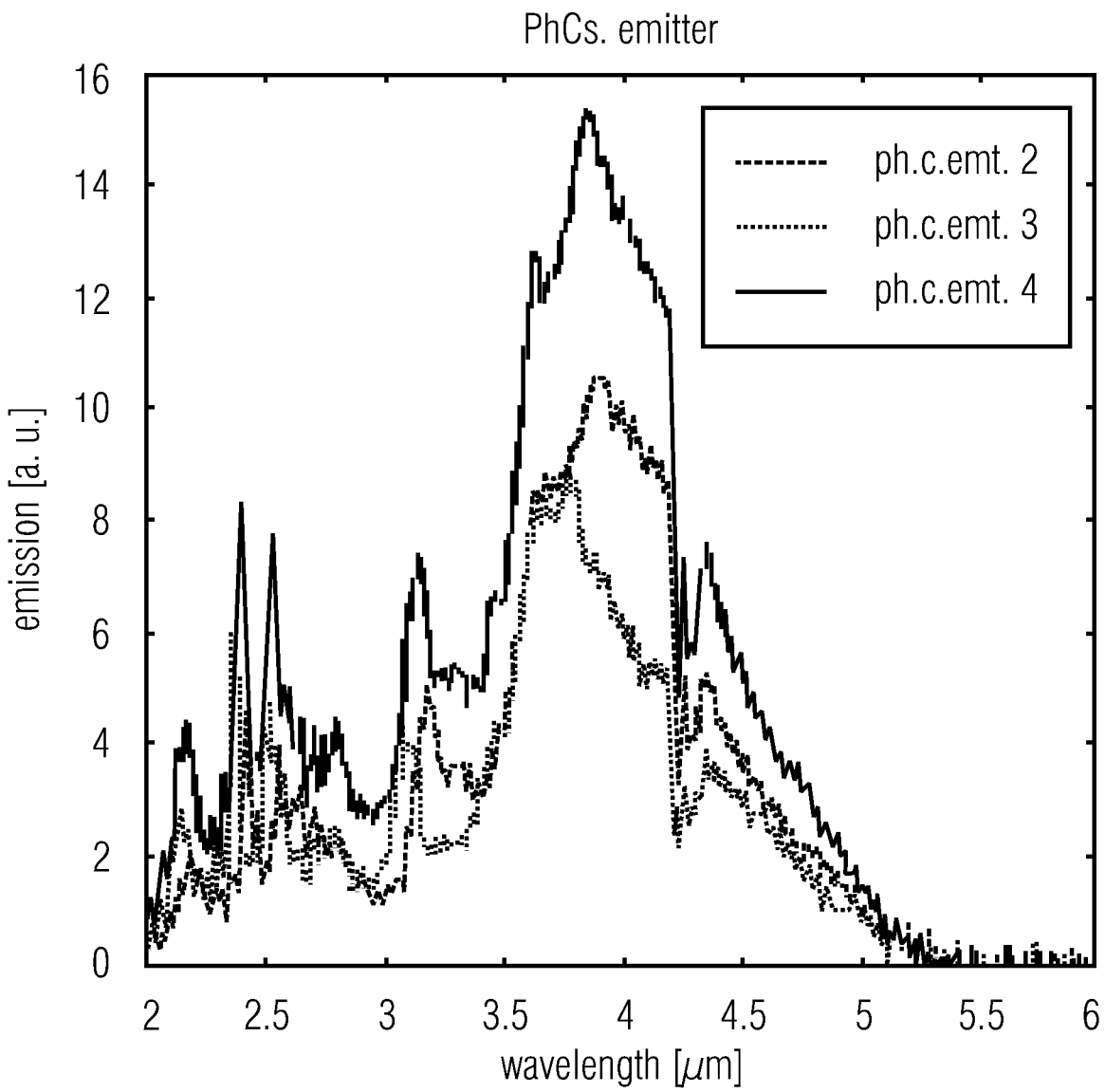
FIG. 8 shows an example of a plot of emissions of photonic crystal emitters over the wavelength according to examples of the disclosure.

FIG. 8 shows an example of a plot of emissions of photonic crystal emitters over the wavelength according to examples of the disclosure. FIG. 7 may show emissions of photonic crystal emitters 700 as shown in FIG. 7 with or without mirror 720. All three emission plots show distinct peaks in arbitrary units (a.u.) around approximately 3.75 μm. A surrounding fluid may interact with the evanescence field of the guided thermal radiation around said wavelength. Therefore, by detecting the guided filtered thermal emission, an information about the surrounding fluid, e.g. its concentration, may be determined.

Figure 9:
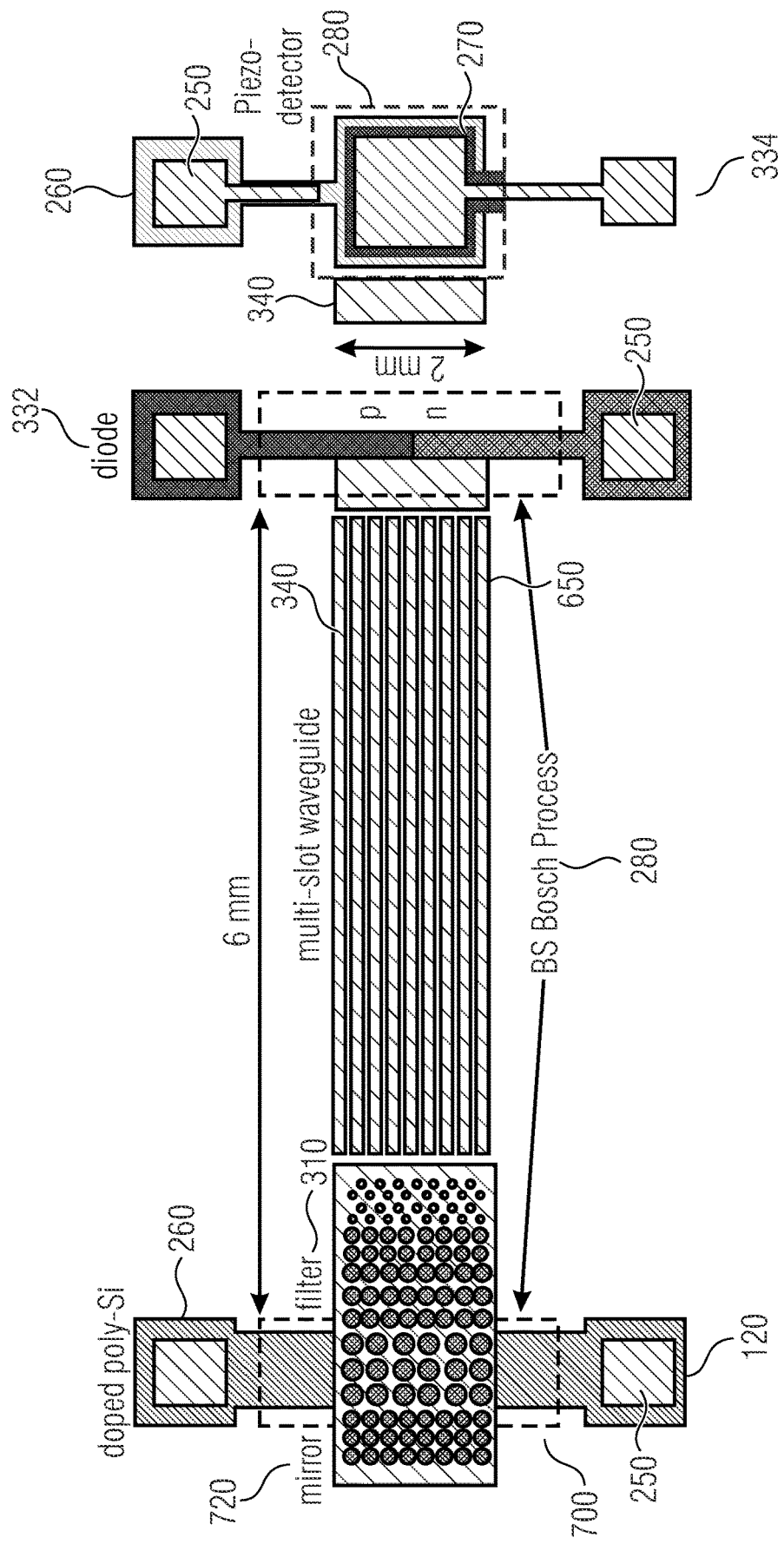
FIG. 9 shows a schematic view of a measurement path of a fluid sensor with a pn junction temperature sensor and an optional piezo detector according to examples of the disclosure.

FIG. 9 shows a schematic view of a measurement path of a fluid sensor with a pn junction temperature sensor and an optional piezo detector according to examples of the disclosure. FIG. 9 may show an, e.g. fully, integrated system or fluid sensor system. FIG. 9 shows a photonic crystal emitter 700 comprising an emitter 120 and a second filter structure 310. The thermal emitter 120 comprises support and/or contact portions 250, a semiconductor strip and a doped Poly-Si material 260. The second filter structure 310 optionally comprises a mirror 720. Alternatively, instead of the mirror 720 a first filter structure 210 may be arranged at the mirror's place, and the emitter 120 may be configured to radiate emission in another radiation emission direction, wherein the other radiation direction is arranged at or is pointing towards the current position of the mirror 720. In other words, the before mentioned reference path may be arranged in this direction, with a first waveguide section coupled to a first filter structure 210. The phonic crystal emitter 700 comprises etched holes for filtering and to provide the mirror characteristics. FIG. 9 shows only a second waveguide section 340 with a multi-slot waveguide 650 providing the measurement path. The fluid sensor further comprises second detector 330, being optionally, a pn junction temperature sensor 332. The detector 120 comprises additionally support and/or contact portions 250. As an example, the distance between emitter 120 and detector 332 may be 6 mm. As another example, the width of the waveguide section 340, parallel to the common system plane, may be 2 mm.

On the right-hand side of FIG. 9 an optional detector 334 is shown which may replace the pn junction temperature sensor 332. Detector 334 is a piezo-detector, or a piezoelectric temperature sensor. The piezo detector may be a 1:1 replacement of the pn junction detector. Optionally, detector 334 may be a pyro-detector. Piezo-detector 334 comprises optionally support and/or contact portions 250, a doped Poly-Si material 260 and an AlN/AlScN (Piezo layer) material 270. The emitter 120 and the detectors 332 or 334 may be formed via a backside Bosch Process 280. In order to increase the resolution of fluid sensors according to the disclosure, the sensor size may be increased (e.g., increasing the area of the waveguide section in addition or correspondingly). In addition, the heater 120, the WG(s) 340, the filter 310, and the detector 332 may form sub-systems of a fluid sensor according to examples of the disclosure.

Figure 10:
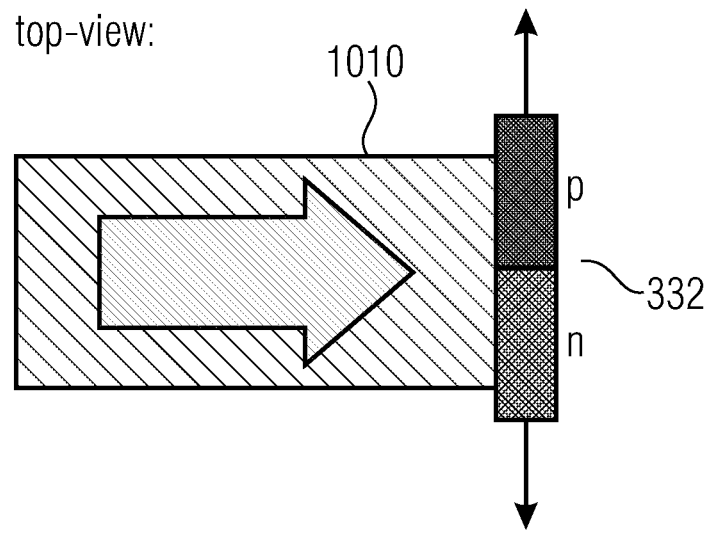
FIG. 10 shows a schematic top view of the pn junction temperature sensor of FIG. 9.

FIG. 10 shows a schematic top view of the pn junction temperature sensor 332, e.g. a diode, of FIG. 9, with a waveguide 1010, e.g. a part of the first and/or second waveguide portion, guiding radiation (represented by arrow) into the detector 332. The sensor may, for example, have a noise equivalent power (NEP) of 1.7e-7 W/Hz$^{1/2}$. A pn junction temperature sensor, e.g. a diode may be processed in a simple way, with low effort and cost.

Figure 11:
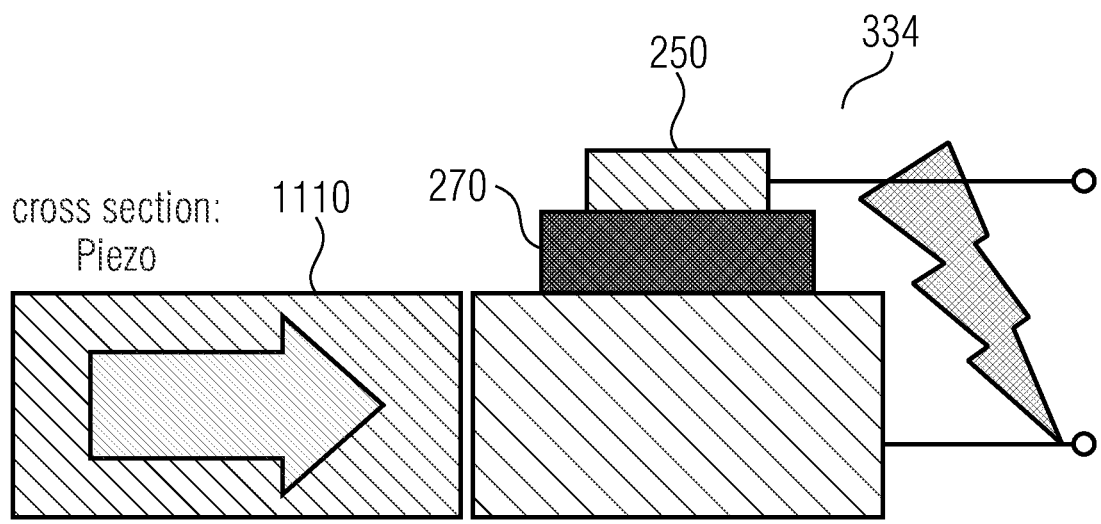
FIG. 11 shows a schematic sideview of the piezo-detector of FIG. 9.

FIG. 11 shows a schematic sideview of the piezo-detector of FIG. 9. FIG. 11 shows waveguide 1110, e.g. a part of the first and/or second waveguide portion, guiding radiation (represented by arrow) into the detector 334. The radiation may heat an absorption layer, e.g., comprising a doped Poly-Si material (not shown). Via the heating of the absorption layer and the detection layer, e.g. comprising an AlN/AlScN material 270, a voltage may be measured between the support and/or contact portions 250. Upper and lower support and/or contact portions represent the support portions of the piezo-detector 334 of FIG. 9. The piezo detector may have a better performance than a pn junction sensor. The sensor may, for example, have a noise equivalent power of 5e-9 W/Hz$^{1/2}$. Optionally, the arrangement shown in FIG. 11 may provide a pyro-detector.

However, it is to be noted that the first detector 130 may as well comprise or be a piezo-detector or a pn junction temperature sensor.

Figure 12:
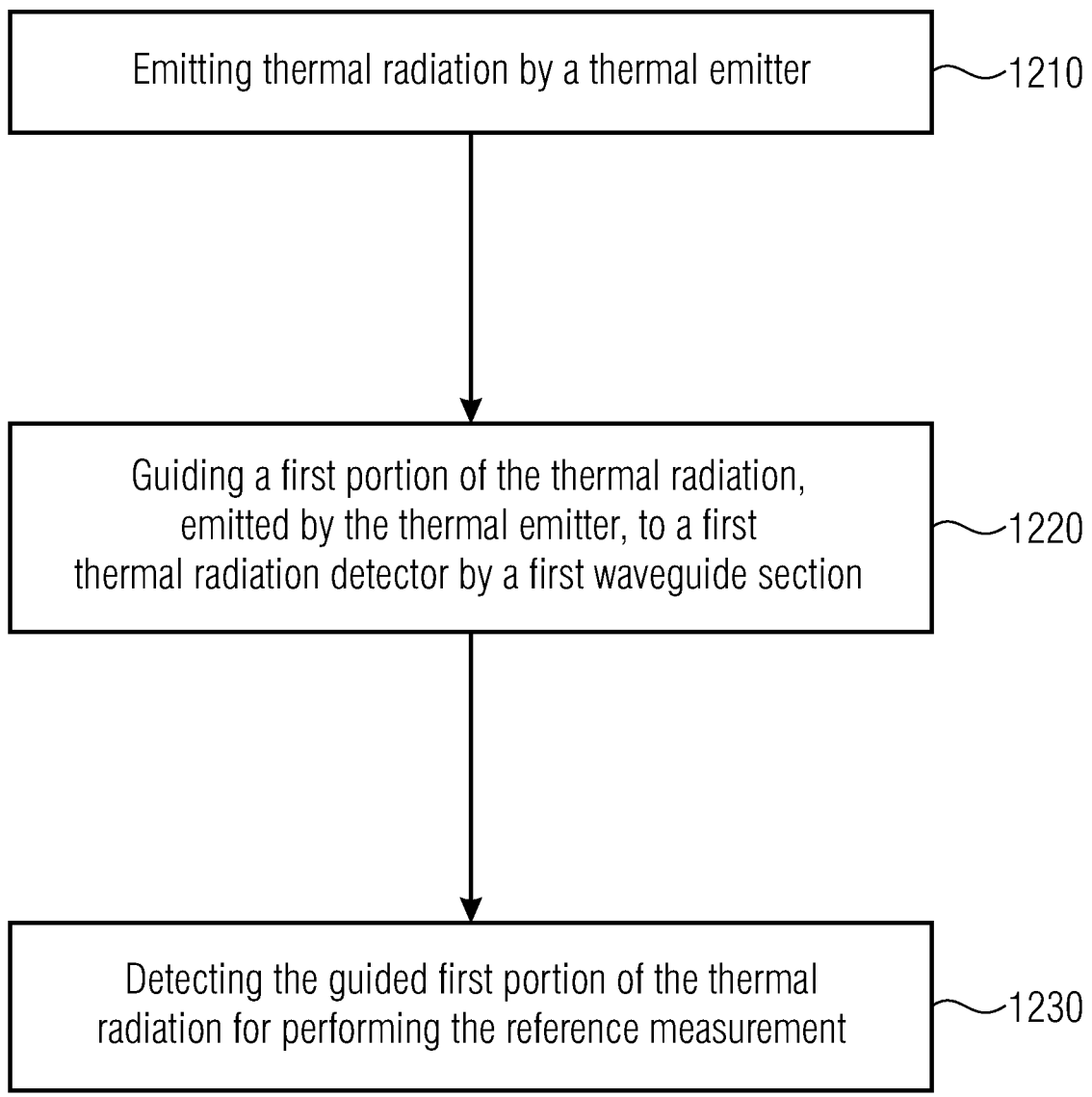
FIG. 12 shows a method for performing a reference measurement according to examples of the disclosure.

FIG. 12 shows a method for performing a reference measurement according to examples of the disclosure. The method 1200 comprises emitting 1210 thermal radiation by a thermal emitter, wherein the thermal emitter is arranged on a top main surface region of a support structure, and wherein the top main surface region of the support structure forms a common system plane. The method 1200 further comprises guiding 1220 a first portion of the thermal radiation, emitted by the thermal emitter, to a first thermal radiation detector by a first waveguide section, wherein the first waveguide section and the first thermal radiation detector are arranged on the top main surface region of the support structure, and wherein at least one part of the first waveguide section is sealed by a cover structure. In addition, the method comprises detecting 1230 the guided first portion of the thermal radiation for performing the reference measurement.

According to further examples of the disclosure, a fluid sensor may comprise an emitter 120, a wave guide (WG) 140, 340, a filter 210, 340, and a detector 130, 330 as components, and may be implemented according to the following principle:

Coupling broad band radiation to a WG 140, 340;

Using a photonic crystal as a filter for specific wavelength (e.g. comprising etched holes);

Using evanescent field for non-dispersive spectroscopy as it interacts with an ambient fluid, e.g. gas;

Converting heat into an electric signal with the detector 130, 330 (detector, for example in the form of a Piezo detector, a Diode detector, or other detector).

According to further examples of the disclosure a fluid sensor may achieve ~300 ppm accuracy at a resolution of ~500 ppm, wherein the first and/or second waveguide section 140, 340 or WG has a width of 500 μm and a length of 5 mm.

Further examples of the disclosure comprise, for example in order to improve performance one or more of the following:

Waveguide sections with a large area, e.g. relative to the area of the common system plane, or in other words big WGs. Bigger WGs may yield even better values (accuracy and resolution)

Waveguide sections with a good coupling efficiency. Improved coupling efficiencies may reduce losses (e.g. in the radiation path: Heater→WG; WG→Detector, e.g. emitter→first waveguide section→first detector and/or emitter→second waveguide section→second detector)

Waveguide sections or WGs with a high evanescence field ratio with low, or at least lower, losses.

In addition or alternatively, examples of the disclosure may comprise one or more of the following advantages:

Form factor (e.g. especially thickness<500 μm)

Fluid sensors according to the disclosure may be fabricated in any shape suitable, because of the ability to specify a certain radiation path via the waveguide sections. Therefore, the fluid sensor may be integrated in for example tight or twisted spaces between other arrangements on a wafer. Moreover, small footprints and thicknesses may be achieved according to the disclosure. In addition, with a monolithic fabrication, only a small amount of wafer-space may be used for the sensor, and a package comprising the sensor may be thin.

8" and 12" fabrication possible

Fluid sensors may be formed on 8" and/or 12" waver. Production on large wavers may reduce the costs for each fluid sensor.

Monolithic approach

Monolithic fabrication enables low cost and high output production of fluid sensors according to the disclosure.

Potential liquid sensor

The surrounding fluid may be a liquid. In general, the fluid sensor may be configured to sense a plurality of gases, or in other words the sensor may be configured to perform multi-gas sensing Potentially more robust Fluid sensors according to the disclosure may be robust. For example, robust with regard to surrounding fluids, or operating time.

Furthermore, fluid sensors according to the disclosure may require a low amount of power, e.g. a reduced amount of power in comparison with equivalent-performance fluid sensors and may provide a reference path.

Moreover, fluid sensors according to examples of the disclosure may be less effected by influences of environmental effects e.g. humidity and/or temperature. The increased electrical efficiency may be able to compensate efficiency losses causes by environmental effects. In addition, said fluid sensors may provide an improved reliability and a lower sensitivity reduction due to aging. Furthermore, a sensor arrangement according to examples of the disclosure may have a long lifetime, e.g. a high number of measurement cycles—especially for the heater.

Another advantage of examples of the disclosure may be the simplicity of the measurement improvement with regard to the information about an ambient fluid, for example in contrast to cases without reference. In such cases, one may work with algorithms in order to correctly interpret the measurement results. This may be more complicated and rather cumbersome. Consequently, examples according to the disclosure may save employing algorithms for interpreting the measurement data. However, usage of algorithms may be applied in order to improve a fluid determination in addition to a correction based on the reference measurement according to examples of the disclosure.

According to further embodiments of the disclosure, the WG of the reference path, e.g. the first waveguide section may be covered in a planar manner, e.g. with a planar cover structure. However, covering the WG in a non-planar manner may represent a weaker influence on the WG itself and, therefore, on the measurement or measurement system. Using a non-planar cover or non-planar cover structure may, e.g. in particular, simplify usage of some forms of WGs (e.g., slot array, or multi-slot). It may even be impossible to implement such WGs in a planar cover.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

The above described examples are merely illustrative for the principles of the present disclosure. It is understood that modifications and variations of the arrangements and the details described herein will be apparent to others skilled in the art. It is the intent, therefore, to be limited only by the scope of the impending patent claims and not by the specific details presented by way of description and explanation of the examples herein.

What is claimed is:

1. A fluid sensor for performing a reference measurement, the fluid sensor comprising:
   a support structure having a top main surface region, wherein the top main surface region of the support structure forms a common system plane of the fluid sensor;
   a thermal emitter on the top main surface region of the support structure, wherein the thermal emitter is configured to emit thermal radiation;
   a first waveguide section on the top main surface region of the support structure;
   a first thermal radiation detector on the top main surface region of the support structure;
   a cover structure on at least one part of the first waveguide section, wherein the cover structure seals a defined atmosphere or a defined fluid in the at least one part of the first waveguide section;
   wherein the first waveguide section is configured to guide a guided first portion of the thermal radiation emitted by the thermal emitter to the first thermal radiation detector;
   wherein the first thermal radiation detector is configured to detect the guided first portion of the thermal radiation for performing the reference measurement; and wherein the guided first portion of the thermal radiation comprises an information about measuring conditions of the fluid sensor.

2. The fluid sensor according to claim 1, wherein the fluid sensor comprises a sealed cavity, and wherein the sealed cavity is arranged between the cover structure and at least one part of the first waveguide section.

3. The fluid sensor according to claim 2,
wherein the first waveguide section is configured for an interaction of an evanescence field of the guided first portion of the thermal radiation with the defined atmosphere or the defined fluid in a predetermined way.

4. The fluid sensor according to claim 1, wherein the fluid sensor comprises a first filter structure and wherein the first filter structure is configured to filter the guided first portion of the thermal radiation emitted by the thermal emitter, and
wherein the first waveguide section comprises the first filter structure;
wherein the thermal emitter comprises the first filter structure;
wherein the first thermal radiation detector comprises the first filter structure; or
wherein the first filter structure is arranged on the top main surface region of the support structure between the thermal emitter and the first waveguide section or between the first thermal radiation detector and the first waveguide section.

5. The fluid sensor according to claim 4, wherein the thermal emitter comprises a semiconductor strip;
wherein the semiconductor strip is configured to emit a broadband thermal radiation, as the thermal radiation;
wherein the first filter structure is an optical filter structure comprising a semiconductor material;
wherein the optical filter structure has a narrow transmission band; and
wherein the optical filter structure is configured to filter the guided first portion of the broadband thermal radiation, emitted by the thermal emitter.

6. The fluid sensor according to claim 5, wherein the fluid sensor comprises a second waveguide section on the top main surface region of the support structure and a second thermal radiation detector on the top main surface region of the support structure;
wherein the second waveguide section is configured to guide a second portion of the thermal radiation, emitted by the thermal emitter, to the second thermal radiation detector;
wherein the second waveguide section is configured to enable an interaction of an evanescence field of the guided second portion of the thermal radiation with a surrounding fluid; and
wherein the second thermal radiation detector is configured to detect the guided second portion of the thermal radiation, in order to determine an information about the surrounding fluid,
based on the interaction of the evanescence field of the guided second portion of the thermal radiation and the surrounding fluid and
based on the guided first portion of the thermal radiation, detected by the first thermal radiation detector.

7. The fluid sensor according to claim 6, wherein the fluid sensor comprises a second filter structure and wherein the second filter structure is configured to filter the second portion of the thermal radiation emitted by the thermal emitter; and
wherein the second waveguide section comprises the second filter structure;
wherein the thermal emitter comprises the second filter structure; and/or
wherein the second thermal radiation detector comprises the second filter structure; or
wherein the second filter structure is arranged on the top main surface region of the support structure between the thermal emitter and the second waveguide section or between the second thermal radiation detector and the second waveguide section.

8. The fluid sensor according to claim 7, wherein the first waveguide section or the second waveguide section comprise at least one of a slab waveguide, a strip waveguide, a slot waveguide, a slot-array waveguide and a multi-slot waveguide; or
wherein the first thermal radiation detector or the second thermal radiation detector comprise at least one of a pyroelectric temperature sensor, a piezoelectric temperature sensor, a pn junction temperature sensor or a resistive temperature sensor.

9. The fluid sensor according to claim 6, wherein the thermal emitter is configured to emit thermal radiation in at least two different radiation emission directions parallel to the system plane and wherein a first radiation emission direction and a second radiation emission direction of the at least two different radiation emission directions are opposite to one another; and
wherein the thermal emitter is configured to emit the guided first portion of the thermal radiation in the first radiation emission direction; and
wherein the thermal emitter is configured to emit the second portion of the thermal radiation in the second radiation emission direction.

10. The fluid sensor according to claim 6, wherein the first or second waveguide section are configured to provide an evanescent field ratio of the guided first and second portion of the thermal radiation of at least 5% and at most 90%.

11. The fluid sensor according to claim 6, wherein the support structure comprises a rigid structure and a substrate on a bottom surface of the rigid structure;
wherein a top surface, opposite to the bottom surface, of the rigid structure is the top main surface region; and
wherein the rigid structure is configured to confine the thermal radiation, radiated by the thermal emitter.

12. The fluid sensor according to claim 11, wherein the substrate comprises at least one substrate cavity; and
wherein the at least one substrate cavity is arranged vertically, with respect to the system plane, below the thermal emitter or below the first thermal radiation detector or the second thermal radiation detector or the first waveguide section or the second waveguide section, for thermal insulation, of the thermal emitter or the first thermal radiation detector or the second thermal radiation detector or the first waveguide section or the second waveguide section, from the substrate.

13. The fluid sensor according to claim 1, wherein the fluid sensor has a footprint in the system plane of less than 45 mm$^2$ of less than 30 mm$^2$ or less than 25 mm$^2$ or a height, wherein the height is orthogonal to the system plane, of less than 1000 μm or less than 950 μm or less than 800 μm.

14. The fluid sensor according to claim 7, wherein at least one of the first thermal radiation detector or the second thermal radiation detector, the first waveguide section or the second waveguide section, the first filter structure or the second filter structure or the thermal emitter is arranged monolithically on the support structure.

15. A method for performing a reference measurement, the method comprising:

emitting thermal radiation by a thermal emitter, wherein the thermal emitter is arranged on a top main surface region of a support structure, wherein the top main surface region of the support structure forms a common system plane;

guiding a first portion of the thermal radiation, emitted by the thermal emitter, to a first thermal radiation detector by a first waveguide section;

wherein the first waveguide section and the first thermal radiation detector are arranged on the top main surface region of the support structure;

wherein at least one part of the first waveguide section seals a defined atmosphere or a defined fluid in a cover structure, wherein the first portion of the thermal radiation comprises an information about measuring conditions of the first thermal radiation detector; and detecting the guided first portion of the thermal radiation for performing the reference measurement.

16. A sensor, comprising:

a support structure having a surface region; and a thermal emitter on the surface region and configured to emit thermal radiation;

a first thermal radiation detector on the surface region;

a first waveguide section on the surface region and configured to guide a first portion of the thermal radiation emitted by the thermal emitter to the first thermal radiation detector;

a cover structure covering at least one part the first waveguide section, wherein the cover structure seals a defined fluid in the at least one part of the first waveguide section; and wherein the first thermal radiation detector is configured to perform a reference measurement on the defined fluid based on detecting the first portion of the thermal radiation.

17. The sensor of claim 16, further comprising:

a sealed cavity arranged between the cover structure and at least one part of the first waveguide section.

18. The sensor of claim 17, wherein the first waveguide section is configured to enable an interaction of an evanescence field of the first portion of the thermal radiation with the defined fluid in a predetermined way, such that the first portion of the thermal radiation comprises an information about the measuring conditions of the first thermal radiation detector.

19. The sensor of claim 16, further comprising:

a first filter structure configured to filter the first portion of the thermal radiation, wherein the first filter structure is included in at least one of: the first waveguide section; the thermal emitter; or the first thermal radiation detector.

20. The sensor of claim 19, wherein the first filter structure is located at least one of: the surface region between the thermal emitter and the first waveguide section; or between the first thermal radiation detector and the first waveguide section.

* * * * *

UNITED STATES PATENT AND TRADEMARK OFFICE
CERTIFICATE OF CORRECTION

PATENT NO. : 12,140,514 B2
APPLICATION NO. : 17/658554
DATED : November 12, 2024
INVENTOR(S) : Stocker et al.

Page 1 of 1

It is certified that error appears in the above-identified patent and that said Letters Patent is hereby corrected as shown below:

In the Claims

In Column 22, in Claim 7, Line 2, after "structure;" delete "and/or".

Signed and Sealed this
Fourth Day of February, 2025

Coke Morgan Stewart
*Acting Director of the United States Patent and Trademark Office*